(12) United States Patent
Wei et al.

(10) Patent No.: US 11,731,197 B2
(45) Date of Patent: Aug. 22, 2023

(54) LIGHT-DRIVEN SYNTHESIS OF PLASMONIC NANOPARTICLES AND NANOMATERIALS

(71) Applicant: University of Florida Research Foundation, Inc., Gainesville, FL (US)

(72) Inventors: Wei David Wei, Gainesville, FL (US); Yueming Zhai, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 17/694,162

(22) Filed: Mar. 14, 2022

(65) Prior Publication Data

US 2022/0234103 A1 Jul. 28, 2022

Related U.S. Application Data

(63) Continuation of application No. 16/303,449, filed as application No. PCT/US2017/034271 on May 24, 2017, now Pat. No. 11,311,940.

(Continued)

(51) Int. Cl.
*B22F 9/24* (2006.01)
*B82Y 5/00* (2011.01)
(Continued)

(52) U.S. Cl.
CPC ............... *B22F 9/24* (2013.01); *B22F 1/054* (2022.01); *B22F 1/056* (2022.01); *B22F 1/0553* (2022.01);
(Continued)

(58) Field of Classification Search
None
See application file for complete search history.

(56) References Cited

U.S. PATENT DOCUMENTS 11,311,940 B2 * 4/2022 Wei .................... C30B 29/66
2006/0207388 A1 9/2006 Mirkin et al.
(Continued)

OTHER PUBLICATIONS

Grzelczak et al., Shape control in gold nanoparticle synthesis, Chemical Society Reviews, Jul. 7, 2008, full text, retrieved from http://pubs.rsc.org/en/content/articlelanding/2008/cs/b711490g/unauth#!divAbstract.

(Continued)

*Primary Examiner* — George Wyszomierski
(74) *Attorney, Agent, or Firm* — Thomas Horstemeyer, LLP

(57) ABSTRACT

In one aspect, the present disclosure pertains to methods of making various noble metal nanoprisms, e.g., gold nanoprisms. In various aspects, the methods can comprise incubating, under dark conditions, a growth solution comprising: (a) a plurality of gold seed structures; (b) a gold precursor, and (c) a photocatalytic intermediary, such that during the incubating step multiply-twinned gold seed structures in the growth solution are preferentially enlarged. The disclosed methods can comprise separating the multiply-twinned gold seed structures from the growth solution based upon the size of the gold seed structures to produce an enriched growth solution. In some aspects, the methods comprise irradiating the enriched growth solution to produce the gold nanoprisms. In some aspects, the disclosed nanoprisms comprise silver.

16 Claims, 31 Drawing Sheets

Related U.S. Application Data

(60) Provisional application No. 62/341,348, filed on May 25, 2016.

(51) Int. Cl.
*C22B 11/00* (2006.01)
*C30B 7/14* (2006.01)
*C30B 29/66* (2006.01)
*B22F 1/054* (2022.01)
*B82Y 30/00* (2011.01)
*B82Y 40/00* (2011.01)

(52) U.S. Cl.
CPC ............... *B82Y 5/00* (2013.01); *C22B 11/04* (2013.01); *C30B 7/14* (2013.01); *C30B 29/66* (2013.01); *B82Y 30/00* (2013.01); *B82Y 40/00* (2013.01)

(56) References Cited

U.S. PATENT DOCUMENTS

| | | |
|---|---|---|
| 2008/0295646 A1 | 12/2008 | Mirkin et al. |
| 2009/0282948 A1 | 11/2009 | Xia et al. |
| 2009/0308202 A1 | 12/2009 | Jin et al. |
| 2010/0133489 A1* | 6/2010 | Mirkin ............... B82Y 30/00 427/595 |
| 2010/0304173 A1 | 12/2010 | Mirkin et al. |
| 2011/0064603 A1 | 3/2011 | Aherne et al. |
| 2012/0134873 A1 | 5/2012 | Orner et al. |
| 2012/0283336 A1 | 11/2012 | Grigorenko et al. |
| 2013/0259903 A1 | 10/2013 | Mortenson et al. |
| 2014/0058028 A1* | 2/2014 | Yoshida ............... C08L 53/00 524/379 |
| 2016/0268962 A1* | 9/2016 | Xue ............... B32B 3/08 |

OTHER PUBLICATIONS

Millstone et al., Colloidal Gold and Silver Triangular Nanoprisms, Small, Mar. 20, 2009, full text, retrieved from http://onlinelibrary.wiley.com/doi/10.1002/smll.200801480/full.

International Search Report and Written Opinion dated Jan. 4, 2018 in co-pending PCT Patent Application No. PCT/US2017/34271.

* cited by examiner

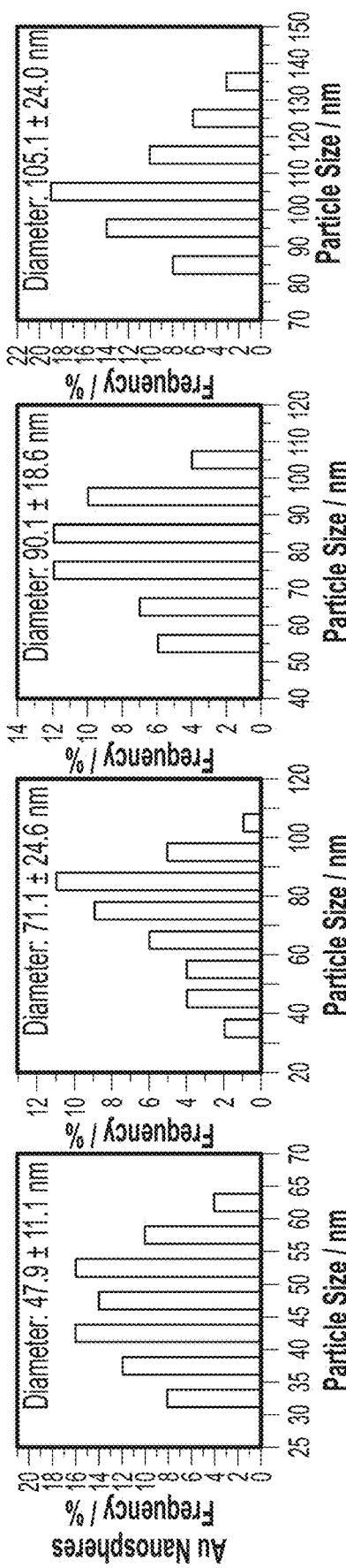
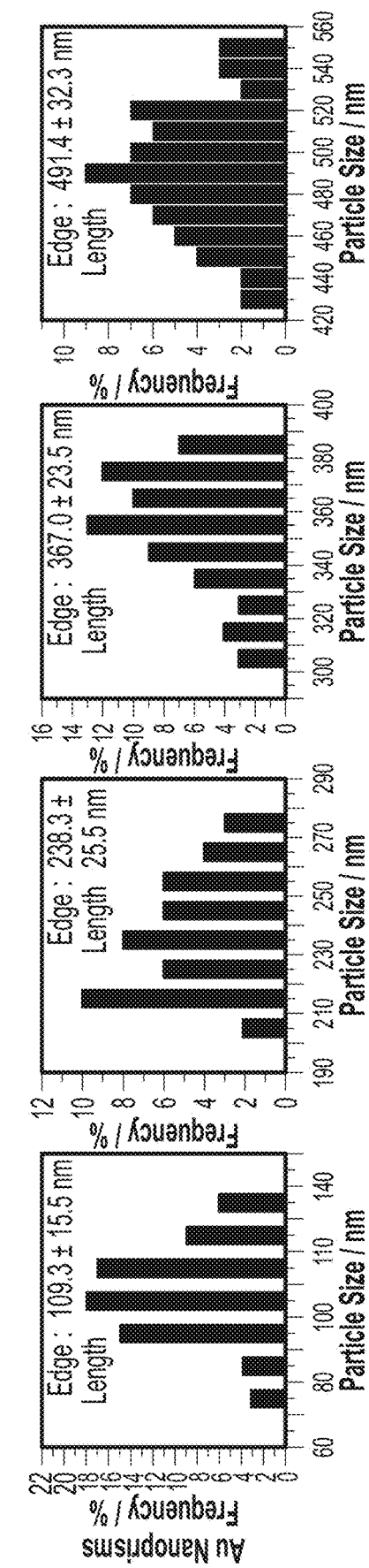

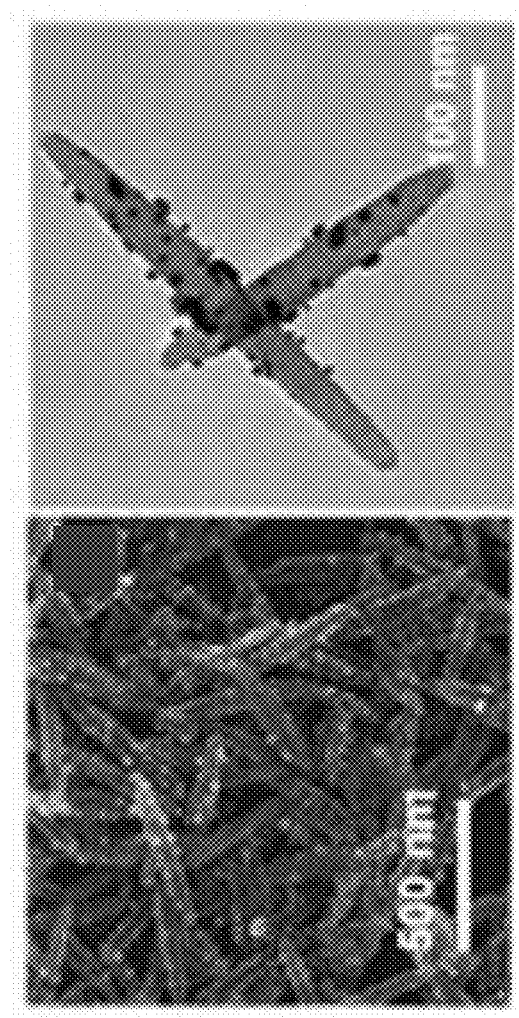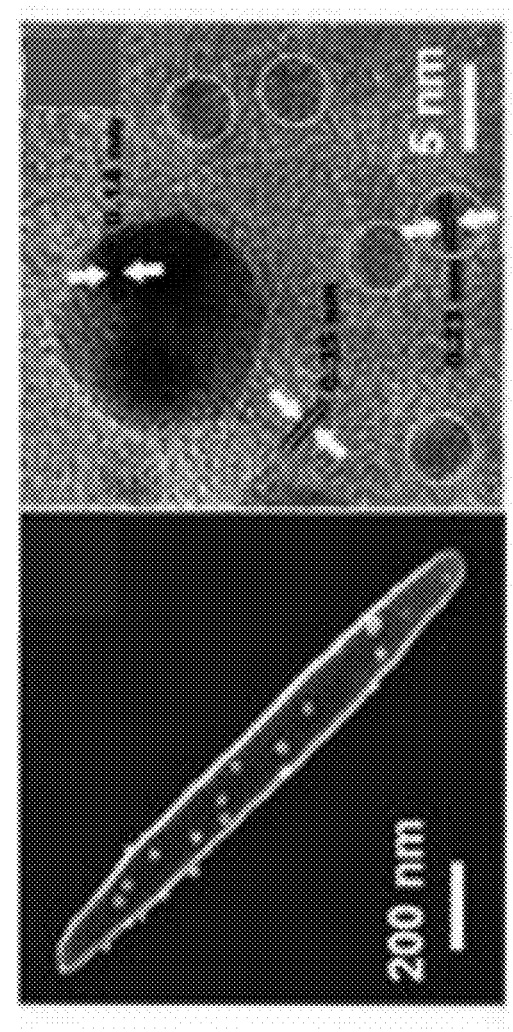
FIG. 32B  FIG. 32C  FIG. 32D  FIG. 32E

LIGHT-DRIVEN SYNTHESIS OF PLASMONIC NANOPARTICLES AND NANOMATERIALS

CROSS-REFERENCE TO RELATED APPLICATIONS

This Application is a Continuation Application that claims benefit of the U.S. National Phase application Ser. No. 16/303,449, filed Nov. 20, 2018, which claims the benefit of International Application No. PCT/US2017/034271, filed May 24, 2017, where International Application No. PCT/US2017/034271 claims the benefit of U.S. Provisional Application No. 62/341,348, filed on May 25, 2016, which is incorporated herein by reference in its entirety.

STATEMENT REGARDING FEDERALLY SPONSORED RESEARCH OR DEVELOPMENT

This invention was made with government support under award FA9550-14-1-0304 awarded by the Air Force Office of Scientific Research, award CHE-1308644 awarded by the National Science foundation, and award CHE-1038015 awarded by the National Science Foundation. The government has certain rights in the invention.

TECHNICAL FIELD

The present disclosure generally relates to methods of making metal nanostructures and metal nanostructures produced therefrom.

BACKGROUND

The prospect of wielding light as a tool for sculpting plasmonic-metal nanostructures has garnered immense scientific interest since the discovery of plasmon-mediated silver (Ag) nanoprism growth in 2001. Unfortunately—despite more than a decade's worth of investigation—the scope of this photochemical strategy remains restricted solely to the synthesis of Ag-based nanostructures (Mirkin et al., *Angew. Chem. Int. Ed.* 2013, 52:13910-13940). It is unknown whether this elemental exclusivity is indicative of a fundamental limitation of plasmonic photochemistry, or is merely a consequence of our insufficient understanding of the plasmon-driven process at the molecular level. Numerous studies have shown that the surface plasmon resonance (SPR) of the nanoparticle seeds must be excited to induce the irreversible photo-oxidation of adsorbed citrate molecules, which then facilitate the concomitant reduction of Ag precursors onto the metal nanocrystal. It has been proposed that these photochemical reactions might be driven by highly energetic or "hot" electron-hole pairs produced via Landau damping during optical excitation of surface plasmons on the metal nanoparticle. Although such a process may occur, a comprehensive description of the molecular mechanisms governing the evolution of anisotropic nanostructures from isotropic seeds remains elusive due to the chemical complexities inherent in the plasmon-mediated synthesis of Ag nanostructures.

Gold (Au) nanostructures boast superior resistance to both chemical oxidation and electron-beam damage as compared to silver. Au is far more important (than Ag) for possible application in medicine and industrial catalysis. However, the plasmon-driven synthesis of anisotropic Au nanostructures has yet to be achieved.

There remains a need for improved methods for plasmon-mediated synthesis of noble-metal nanostructures that can be applied to metals other than silver, such as gold, and that overcome the aforementioned deficiencies.

SUMMARY

Methods of making various noble metal nanoprisms are provided. Noble metal nanoparticles can include ruthenium, rhodium, palladium, osmium, iridium, platinum, gold, mercury, rhenium, copper, or a combination thereof. In various aspects, the nanoprisms do not include silver. In one or more aspects, the nanoprisms are gold nanoprisms.

In various aspects, methods of making noble metal nanoprisms are provided. The methods can include irradiating a solution comprising a plurality of seed structures, a noble metal precursor, and a photocatalytic intermediary to produce the noble metal nanoprisms. The solution can be a growth solution or, in some aspects, the solution is an enriched growth solution. The enriched growth solution can include a growth solution wherein multiply-twinned seed structures have been removed from the growth solution. In various aspects, the enriched growth solution can be produced by incubating, under dark conditions, the growth solution, wherein during the incubating step multiply-twinned seed structures in the growth solution are preferentially enlarged, and then separating the multiply-twinned seed structures from the growth solution based upon the size of the seed structures to produce an enriched growth solution.

In one or more aspects, methods of making gold nanoprisms are provided, the methods including (i) incubating, under dark conditions, a growth solution containing a plurality of gold seed structures, a gold precursor, and a photocatalytic intermediary, wherein during the incubating step multiply-twinned gold seed structures in the growth solution are preferentially enlarged. In various aspects, the methods can include separating the multiply-twinned gold seed structures from the growth solution based upon the size of the gold seed structures to produce an enriched growth solution. In some aspects, the methods include irradiating the enriched growth solution to produce the gold nanoprisms.

The solutions can include a noble metal precursor. For example, for producing nanoprisms containing gold, the solutions can include a gold precursor such as $HAuCl_4$, $AuCl_3$, or $Au(O_2CCH_3)_3$. In various aspects, the noble metal precursor is a salt of the noble metal, such as a chloride salt.

The methods can be performed under a variety of conditions. In various aspects, the incubating step is performed at an elevated temperature from about 30° C. to about 40° C. In some aspects, the growth solution has an acidic pH, e.g. the growth solution has a pH of about 3.0 to 6.0. In one or more aspects, the irradiating step includes irradiating with light having a wavelength from about 500 nm to 600 nm, and the nanoprisms have an average edge length of about 400 nm to 600 nm. In some aspects, the irradiating step includes irradiating with light having a wavelength from about 600 nm to 700 nm, and the nanoprisms have an average edge length of about 200 nm to 400 nm.

A variety of photocatalytic intermediaries can be used in the methods described. In various aspects, the photocatalytic intermediary is positively charged or is made to be positively charged by adjusting the pH of the solution. The photocatalytic intermediary can include a lactam ring such as a γ-lactam ring. In various aspects, the photocatalytic intermediary includes n-methyl-2-pyrrolidone such as in the polymer polyvinylpyrrolidone (PVP). The growth solution can, in various aspects, also include a salt such as sodium iodide.

The methods can be used to make a variety of nanoprisms from a variety of seed structures. In various aspects, the seed structures include one or more of single-crystalline structures, planar-twinned structures, penta-twinned structures, and multiply-twinned structures. The seed structures can be small, e.g. having an average size of about 5 nm to 15 nm. The nanoprisms produced can include a variety of nanoprism geometries. In various aspects, the nanoprisms include hexagonal nanoprisms and triangular nanoprisms. The nanoprisms can be made with a variety of thicknesses, e.g. about 10 nm to 30 nm or about 30 nm to 50 nm.

The nanoprisms can, in various aspects, be produced with high yield, e.g. about 80%, 90%, or more. In various aspects, one or more noble metal nanoprisms are provided made by the methods described herein.

Other systems, methods, features, and advantages of the disclosed methods and compositions will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1A is a TEM image of the Au nanocrystals used as plasmonic seeds for the growth of Au nanostructures. FIG. 1B is a graph of the extinction spectrum of the Au seed solution (line) displaying a prominent SPR feature at 512 nm. The amount of Au precursor (HAuCl$_4$) consumed in the growth solution after 1 h of irradiation with various excitation wavelengths was correlated with the SPR of these Au seeds (circular data points). FIG. 1C is an SEM image of the final products obtained via irradiation of the growth solution with $\lambda_{inc}$=500±10 nm light for 2 h. FIG. 1D is a graph of the influence of incident light power on the amount (μmol) of HAuCl$_4$ consumed in the growth solution during 1 h of irradiation ($\lambda_{inc}$=500±10 nm). All error bars in FIG. 1B and FIG. 1D indicate one standard deviation about the mean from three independent trials.

FIGS. 2A-2E are ADF-STEM image with corresponding EELS maps acquired from a single Au hexagonal nanoprism. FIGS. 2F-2J are ADF-STEM images with corresponding EELS maps acquired from a single Au triangular nanoprism. Scale bars in STEM images FIG. 2A and FIG. 2F also apply to their respective EELS maps. The common EELS intensity scale is linear and expressed in arbitrary units. FIGS. 2K-2P are SEM images of Au nanoprisms before irradiation (FIG. 2K, FIG. 2M, and FIG. 2O) and after irradiation (FIG. 2L, FIG. 2N, FIG. 2P) with various incident-light wavelengths ($\lambda_{inc}$) while immobilized on a Si substrate: (FIG. 2K, FIG. 2L) 520 nm (2.38 eV), (FIG. 2M, FIG. 2N) 780 nm (1.59 eV), (FIG. 2O, FIG. 2P) 960 nm (1.29 eV). Dashed white lines indicate the initial Au nanoprism dimensions to aid comparison. All scale bars represent 100 nm.

FIG. 3A is an SEM image of Au nanostructures obtained after 2 h of photochemical growth. FIGS. 3B-3C are NanoSIMS images obtained from the Au nanostructures in (FIG. 3A) showing the elemental distributions of $^{197}$Au$^-$ signals (FIG. 3B) and $^{12}$C$^{14}$N$^-$ signals (FIG. 3C). The scale bar in (FIG. 3A) also applies to images (FIG. 3B) and (FIG. 3C). FIGS. 3D-3E are SEM images of individual Au nanoprisms and pseudo-spherical nanoparticles before growth (FIG. 3D) and after growth (FIG. 3E) under $\lambda_{inc}$=500±10 nm light irradiation for 30 min. Dashed white and red lines indicate the initial dimensions of the nanoprisms and nanoparticles, respectively.

FIG. 4A is an SEM image of Au hexagonal nanoprisms obtained after 2 h of irradiation following the seed separation method. The insets in FIG. 4A show (i) a high-magnification SEM image of a single hexagonal nanoprism and (ii) a NanoSIMS image showing the elemental distribution of $^{12}$C$^{14}$N$^-$ signals (green) from adsorbed PVP on a hexagonal nanoprism. FIG. 4B is an SEM image of Au triangular nanoprisms obtained after 2 h of irradiation with the addition of iodide (I$^-$) to the growth solution following the seed separation method. The insets in FIG. 4B show (i) a high-magnification SEM image of a single triangular nanoprism and (ii) a NanoSIMS image showing the elemental distribution of $^{12}$C$^{14}$N$^-$ signals (green) and $^{127}$I$^-$ signals (blue) from a triangular nanoprism. The scale bars in all insets represent 200 nm.

FIG. 5A is a TEM image of a Au nanoprism produced by irradiating the growth solution for 2 h with 500±10 nm light. The inset shows an HRTEM image of the Au nanoprism surface, which displays a lattice spacing of 0.24 nm, consistent with the {111} facet. FIG. 5B demonstrates a typical selected area electron diffraction (SAED) pattern taken from an individual Au nanoprism supported on the TEM grid. The spot (circle) was indexed to the {220} reflection, the spot (box) was assigned to the {422} reflection, and the spot (triangle) corresponds to the formally forbidden ⅓ {422} reflection. FIG. 5C is an AFM image of a single Au nanoprism. FIG. 5D is a cross-sectional scan of the Au nanoprism along the blue line shown in (FIG. 5C) indicating a nanoprism thickness of ca. 22 nm.

FIGS. 6A-6M depict time-dependent evolution of Au nanostructures. Extinction spectra of the growth solution with (FIGS. 6B-6E) SEM images and (FIGS. 6F-6M) corresponding size distribution histograms taken every 30 min to monitor the photochemical growth of Au nanostructures under visible-light excitation ($\lambda_{inc}$=500±10 nm) over the course of the 2 h reaction. These spectra exhibit two distinctive features in the visible ($\lambda$max~550 nm) and near-infrared ($\lambda_{max}$>1100 nm) regions attributed to the SPR of the Au nanospheres and the Au nanoprisms, respectively.

(FIG. 8A) single-crystalline, (FIG. 8B) planar-twinned, (FIG. 8C) penta-twinned, and (FIG. 8D) complex multiply-twinned structure. Dashed white lines serve as a guide to highlight the twin boundaries. All scale bars represent 2 nm.

FIG. 9A is a graph of the extinction spectra of growth solution with (FIGS. 9B-9G) corresponding SEM images after 2 h of irradiation with the following incident wavelengths ($\lambda$inc): (FIG. 9B) 480±10 nm, (FIG. 9C) 500±10 nm, (FIG. 9D) 520±10 nm, (FIG. 9E) 540±10 nm, (FIG. 9F) 580±10 nm, and (FIG. 9G) 620±10 nm.

FIG. 11A is a gas chromatogram spectrum obtained from the growth solution before light irradiation. Only methanol ($CH_3OH$) is observed. FIG. 11B is a spectrum obtained from the same solution after 2 h of light irradiation with 500±10 nm light, showing a second feature indicative of formaldehyde ($CH_2O$). FIG. 11C is a gas chromatogram spectrum obtained from a mixture of methanol ($CH_3OH$), formic acid (CHOOH), and formaldehyde ($CH_2O$) for comparison. These results confirm that formaldehyde is the photochemical byproduct of methanol oxidation.

FIGS. 12A-12D are SEM images of the Au nanoprisms produced using (FIG. 12A) methanol, (FIG. 12B) formaldehyde, (FIG. 12C) citrate, or (FIG. 12D) ethanol as a hole scavenger. All scale bars represent 500 nm. Au nanoprisms were produced regardless of which hole scavenger was used, confirming that the sacrificial reagent exerts no influence over the nanoprism morphology.

FIG. 13A is a graph of the extinction spectrum of the final products obtained after 2 h of irradiation with 500±10 nm light without methanol in the growth solution. Only the absorption features of the initial Au precursor were observed, indicating no appreciable growth occurred in the absence of the hole scavenger methanol. FIGS. 13B-13C are SEM images of single-nanoparticle growth experiments conducted with a collection of Au nanospheres and a single Au nanoprism immobilized on a Si substrate before (FIG. 13B) and after irradiation with 500±10 nm light for 2 h (FIG. 13C). Both scale bars represent 200 nm. In agreement with the results presented in (FIG. 13A), no noticeable growth occurred without methanol present as a hole scavenger to complete the photocatalytic cycle. These results further confirm that PVP itself is incapable of reducing the $HAuCl_4$ precursor in the absence of a hole scavenger under these experimental conditions.

(FIG. 15A) pH 3.0, (FIG. 15B) pH 5.0, (FIG. 15C) pH 6.0, (FIG. 15D) pH 7.0, and (FIG. 15E) pH 9.0.

FIGS. 19A-19D are SEM images of Au nanoprisms produced using the standard 0.4 mg/mL PVP (FIG. 19A and FIG. 19B) or 8 mg/mL PVP in the growth solution (FIG. 19C and FIG. 19D).

FIG. 20A is an SEM image of the thicker Au nanoprism sample obtained with 8 mg/mL PVP characterized by NanoSIMS. FIG. 20B depicts the elemental distribution of gold ($^{197}Au^-$) in the sample. FIG. 20C depicts the elemental distribution of $^{12}C^{14}N^-$ in the sample, showing signals from the entire surface of each Au nanoprism. These results confirm that the physical location of PVP on the nanoprism surface is regulated by the PVP concentration. More importantly, these data confirm that the physical location of PVP determines the growth direction of the Au nanoprisms. The scale bar in (FIG. 20A) applies to FIGS. 20A-20C.

FIGS. 21A-21D are HRTEM images of Au nanoparticles showing planar-twinned (FIG. 21A and FIG. 21B) and penta-twinned (FIG. 21C and FIG. 21D) nanocrystals containing defects such as surface steps, kinks, and stacking-faults. All scale bars represent 1 nm. Dashed white lines serve as a guide to highlight the twin boundaries. The red and blue lines indicate steps near twinned boundaries (FIG. 21A to FIG. 21C), and the area within the blue rectangle (FIG. 21D) shows a kink of the crystal lattice.

FIGS. 22A-22D are SEM images of Au nanoparticles obtained after incubation in the dark for (FIG. 22A) 2 h, (FIG. 22B) 6 h, (FIG. 22C and FIG. 22D) 12 h along with (FIG. 22E) corresponding extinction spectra after 12 h, and (FIG. 22F) size distribution histogram after 12 h. In FIG. 22A only small Au nanospheres were obtained after 2 h of incubation in the dark. In FIG. 22B, after 6 h, larger pseudo-spherical nanoparticles and many decahedral structures were identified (red circles). In FIG. 22C, large (d~100 nm) spherical Au nanoparticles were obtained if the dark reaction was extended to 12 h; however, no Au nanoprisms were observed. In FIG. 22D, high magnification image showing multiply-twinned structures were the dominant nanocrystals produced during the 12 h dark incubation period. These results show that the reduction of $AuCl_4^-$ by methanol in the dark is driven by the innate surface activity of the Au nanostructures. For multiply-twinned Au nanoparticles (e.g. penta-twinned decahedrons) the five-fold twin boundaries exhibit lattice rotation coupled with shear strains that elevate the surface energy of the metal nanocrystal. These multiply-twinned seeds thereby inherently possess a large proportion of active surfaces for $AuCl_4^-$ reduction, leading to faster growth kinetics in the dark compared to the more stable planar-twinned nanoparticles. FIG. 22E is a graph of the extinction spectrum of the growth solution after 12 h in the dark exhibiting a single feature at ca. 588 nm due to the Au nanoparticles, confirming the absence of nanoprisms. FIG. 22F is a histogram of Au nanoparticle size exhibiting a roughly Gaussian distribution with an average diameter of d=97±19 nm.

FIG. 24A is a TEM image of Au nanoseeds after 12 h dark reaction. Besides the large Au nanoparticles (average particle size was 97±23 nm), there were still many tiny Au nanoparticles present (highlighted by the indicated circle). FIG. 24B is a HRTEM image of these tiny Au nanoparticles (average particle size was 15±1 nm) shows an increase in nanocrystals containing planar-twinned boundaries (highlighted by indicated arrows) relative to the initial Au seed solution.

FIGS. 25A-25B are SEM images of a single Au nanoprism and several pseudo-spherical nanoparticles (FIG. 25A) before and (FIG. 25B) after growth in the dark for 6 h. Both scale bars represent 100 nm. White and red dashed lines were added to illustrate the initial dimensions of the Au nanoprism and nanospheres, respectively. These images reveal that only the spherical nanoparticles grew to a noticeable extent in the dark. This experiment further shows that the growth process in the dark is seed-mediated, as no new nanoparticles were observed on the bare Si substrate.

FIG. 26 is a graph of the transient open-circuit voltage $[V_{oc}(t)]$ rise/decay from photoelectrodes composed of either planar-twinned Au nanoprisms (line as indicated on the graph) or multiply-twinned Au nanoparticles (line as indicated on the graph) during excitation/termination of visible-light irradiation ($\lambda inc>495$ nm). This electrochemical technique was used to demonstrate the influence of nanocrystal twinning on the plasmon-driven growth of Au nanostructures. The separation of these two nanocrystals in high purity was accomplished via the method outlined in FIG. 27. These data show that the planar-twinned nanoprisms exhibit larger photovoltages ($V_{ph}\sim60$ mV) than the multiply-twinned nanocrystals ($V_{ph}\sim30$ mV), in agreement with our expectation that the planar-twinned nanoprisms should sustain a greater number of hot carriers capable of catalyzing $HAuCl_4$ reduction under steady-state illumination.

FIGS. 29A-29D are SEM images showing the yield of Au nanoprisms obtained after reaction in the dark for (FIG. 29A) 0 h, (FIG. 29B) 12 h, (FIG. 29C) 24 h, and (FIG. 29D) 36 h. The % yield (by shape) of nanoprisms is clearly dependent on the amount of dark reaction time, as noted in the upper right-hand corner of each image. This dark incubation period can impact the ability to obtain high yields of Au nanoprisms, as it excludes the multiply-twinned nanocrystals from the starting seed solution prior to irradiation. All scale bars represent 2 µm.

FIG. 31A is an SEM image of the Au nanoprisms inspected by NanoSIMS. FIG. 31B is an elemental distribution of gold ($^{197}Au^-$) signals detected from the sample. FIG. 31C is an elemental distribution of $^{12}C^{14}N^-$ signals detected from the sample. FIG. 31D is an elemental distribution of iodide ($^{127}I^-$) signals detected from the sample. FIG. 31E is an overlay of both $^{12}C^{14}N^-$ and $^{127}I^-$ signals from (FIG. 31C) and (FIG. 31D) to show the physically separate locations of these two complementary ligands on the Au nanoprism surface. Scale bar in (FIG. 31A) applies to images FIGS. 31A-31E.

FIGS. 32A-32E depict photodeposition of platinum onto Au—$TiO_2$ nanorod heterostructures. FIG. 32A shows representative UV-Vis extinction spectra of Ti—$O_2$ nanorods and Au—$TiO_2$ heterostructures; FIG. 32B shows a representative SEM image of Au—$TiO_2$ heterostructures; FIG. 32C shows a representative SEM image of Au—$TiO_2$ heterostructures; FIG. 32D shows a representative TEM image of a single Au—$TiO_2$ heterostructure; and FIG. 32E shows a representative HRTEM image of a single Au—$TiO_2$ heterostructure.

DETAILED DESCRIPTION

Figures 1A, 1B, 1C, 1D:
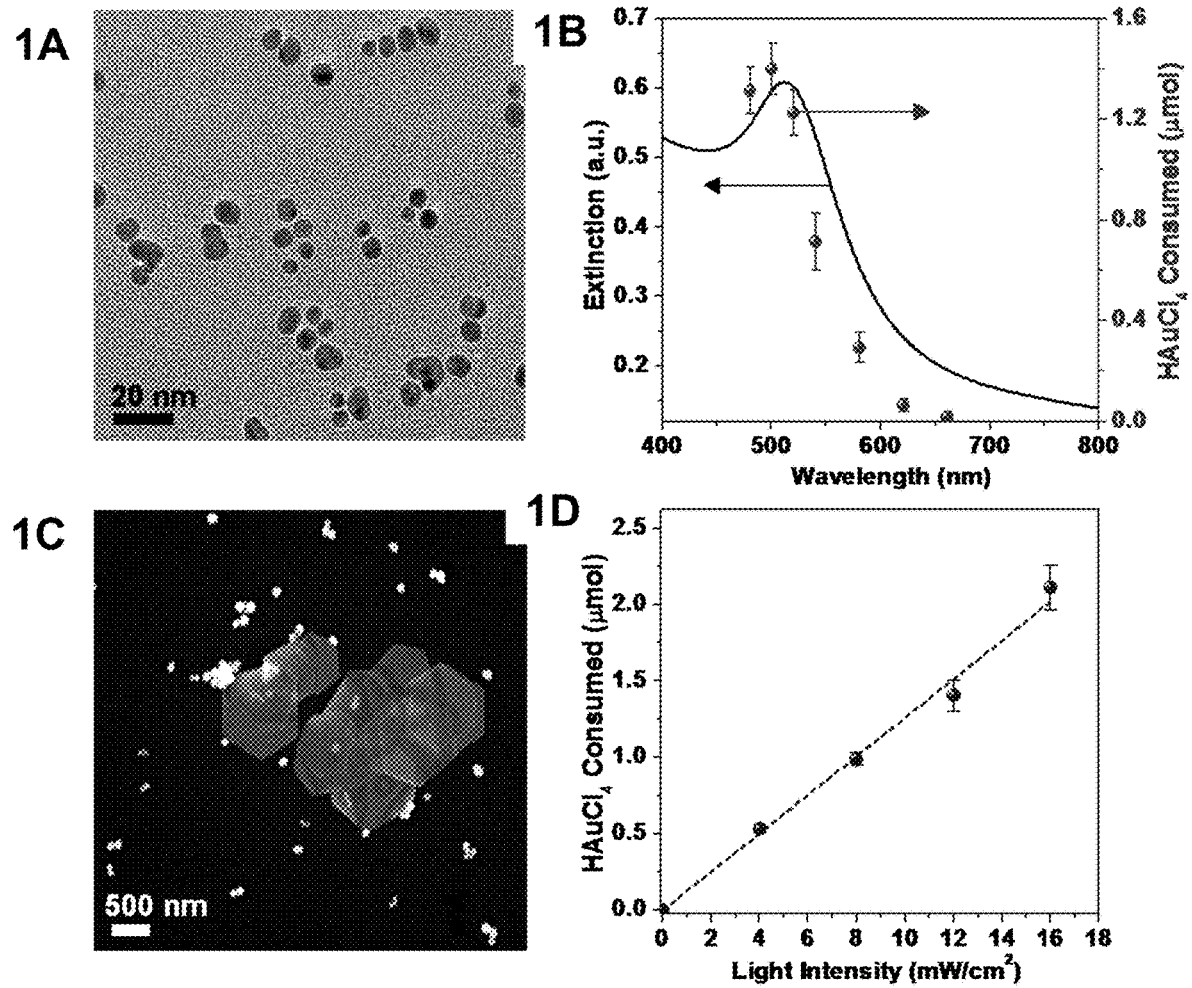
FIGS. 1A-1D depict plasmon-driven synthesis of Au nanostructures.
Figures 2A, 2P:
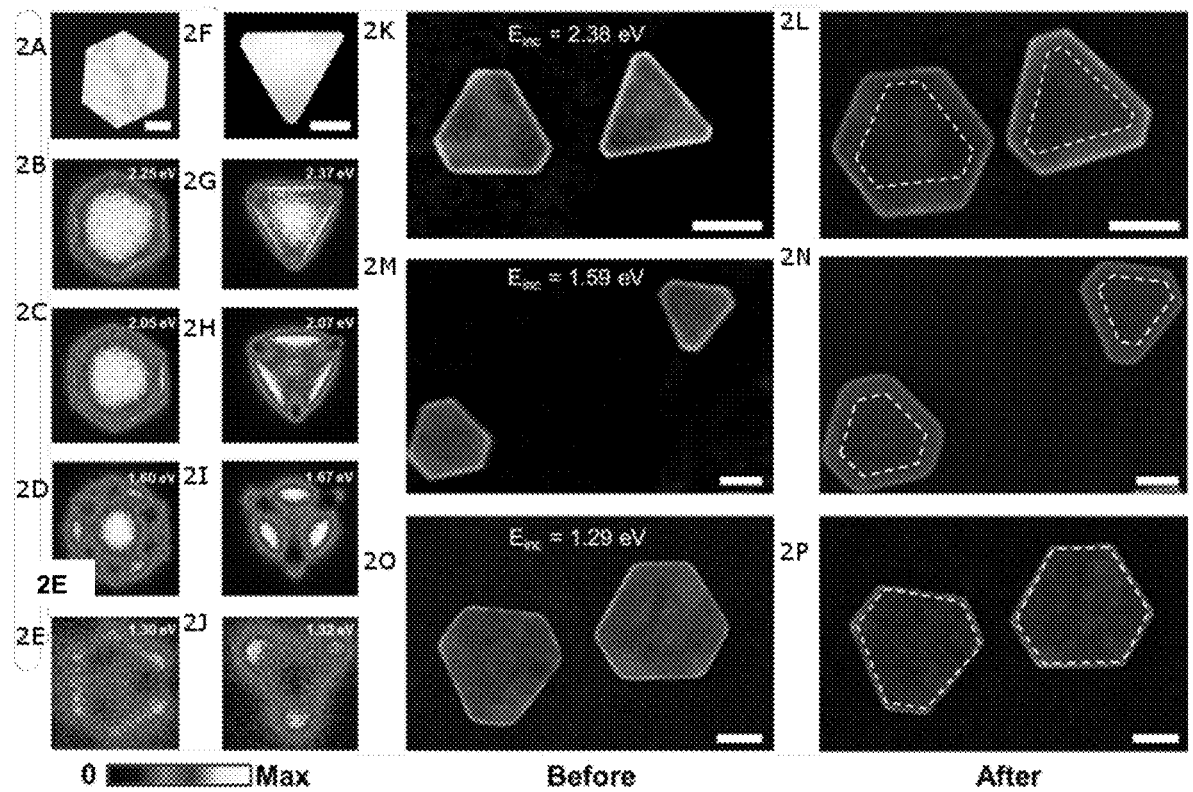
FIGS. 2A-2P demonstrate the influence of plasmonic hot spots on Au nanoprism growth.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term nanoprism, as used herein, refers to any nanoparticle having at least two non-parallel faces that share a common edge. Nanoprisms can include cubic prisms, rectangular prisms, pentagonal prisms, hexagonal prisms, or the like.

Methods of Making Noble Metal Nanoprisms and Nanoprisms Produced Therefrom

Various methods of making noble metal nanoprisms and nanoprisms produced therefrom are provided. The methods can be applied to a variety of noble metal systems, including one or more of ruthenium, rhodium, palladium, osmium, iridium, platinum, gold, mercury, rhenium, copper, and a combination thereof. In one or more aspects, the noble metals do not include silver. In some embodiments, the noble metals include gold. The nanoprisms can be produced with high yield, e.g. about 60%, about 70%, about 80%, about 85%, about 90%, about 95%, or more.

In various aspects, the methods include using a growth solution. In some aspects, the growth solution is irradiated, while in some embodiments the growth solution is enriched prior to irradiating. The growth solution can include a plurality of seed structures, a noble metal precursor, and a photocatalytic intermediary. For example, in some aspects the noble metal nanoprisms are gold nanoprisms and the growth solution includes a plurality of gold seed structures, a gold precursor, and a photocatalytic intermediary.

In various aspects, the methods include irradiating the growth solution to produce the noble metal nanoprisms. In some aspects, the growth solution is enriched and the methods include irradiating the enriched growth solution. The growth solution can be enriched by incubating the growth solution under dark conditions, wherein during the incubating step multiply-twinned seed structures in the growth solution are preferentially enlarged. The methods can then include separating the multiply-twinned seed structures from the solution based upon the size of the seed structures to produce an enriched growth solution. For example, the multiply-twinned seed structures can be large enough to separate using centrifugation. For example, when the nanoprisms include gold nanoprisms, the methods can include incubating the growth under dark conditions to preferentially enlarge the multiply-twinned gold seeds and separating the multiply-twinned gold seeds from the growth solution based upon size. The incubating step can be performed at a variety of temperatures, e.g. about 25° C. to about 50° C., about 30° C. to about 50° C., about 30° C. to about 40° C., about 30° C. to about 35° C., or about 35° C. to about 40° C.

The methods can include irradiating the growth solution, e.g. with a specific wavelength or wavelengths of light. In some aspects, the irradiating step is applied to the growth solution without enrichment while in other embodiments the growth solution is enriched prior to irradiation. The irradiating step can include radiating with light having a wavelength of about 350 nm to 450 nm, about 400 nm to 500 nm, about 450 nm to 550 nm, 500 nm to 600 nm, about 550 nm to 650 nm, about 600 nm to 700 nm, about 650 nm to 750 nm, or about 700 nm to 800 nm. The irradiating step can be performed for about 1 hour, about 2 hours, about 3 hours, or more.

The growth solution can include a plurality of seed structures. In various aspects, the seed structures are gold seed structures. The seed structures can include one or more of ruthenium seed structures, rhodium seed structures, palladium seed structures, osmium seed structures, iridium seed structures, platinum seed structures, gold seed structures, mercury seed structures, rhenium seed structures, and copper seed structures. The seed structures can include one or more of single-crystalline structures, planar-twinned structures, penta-twinned structures, and multiply-twinned structures. The seed structures can have an average size of less than about 5 nm, about 5 nm to 50 nm, about 5 nm to 25 nm, about 5 nm to 10 nm, about 10 nm to 15 nm, about 5 nm to 15 nm, about 10 nm to 20 nm, about 15 nm to 25 nm, or about 20 nm to 30 nm.

The growth solution can include a noble metal precursor such as a gold precursor. Gold precursors can include $HAuCl_4$, $AuCl_3$, and $Au(O_2CCH_3)_3$. In various aspects, the noble metal precursor includes a salt of the noble metal, e.g. a ruthenium salt, rhodium, palladium salt, osmium salt, iridium salt, platinum salt, gold salt, mercury salt, rhenium salt, or a copper salt. The salt can include, for example, a chloride or other halide salt.

The growth solution can include a photocatalytic intermediary. In various aspects, the photocatalytic intermediary is polyvinylpyrrolidone (PVP). The photocatalytic intermediary can include n-methyl-2-pyrrolidone or another lactam ring. The lactam ring can be a γ-lactam ring. The photocatalytic intermediary can have a positive charge, e.g. in some embodiments the pH of the growth solution is adjusted to ensure the photocatalytic intermediary has a positive charge. In some embodiments, the growth solution has an acidic pH of about 2.0 to 6.9, about 2.0 to 6.0, about 3.0 to 6.0. about 3.0 to 5.0, about 3.0 to 4.0, about 4.0 to 5.0, or about 5.0 to 6.0. The growth solution can also include sodium iodide.

The noble metal nanoprisms can be a variety of prismatic structures, including hexagonal nanoprisms and trigonal nanoprisms. The nanoprisms can have an average edge length of about 200 nm to 1000 nm, about 200 nm to 800 nm, about 200 nm to 600 nm, about 200 nm to 400 nm, about 300 nm to 500 nm, about 400 nm to 600 nm, about 500 nm to 700 nm, or about 600 nm to 800 nm. The nanoprisms can have an average thickness of about 10 nm to 100 nm, about 10 nm to 75 nm, about 10 nm to 50 nm, about 10 nm to 40 nm, about 10 nm to 30 nm, about 30 nm to 50 nm, about 40 nm to 60 nm, or about 50 nm to 70 nm.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Materials

Tetrachloroauricacid ($HAuCl_4$), sodium iodide (NaI), polyvinylpyrrolidone (PVP, MW=40,000), methanol (99.8%), formaldehyde (36.5-38% in $H_2O$), formic acid (>95%), ethanol, hydrochloric acid (HCl), and sodium borohydride ($NaBH_4$) were purchased from Sigma Aldrich (St. Louis, Mo.). Trisodium citrate ($Na_3C_6H_5O_7$) and sodium hydroxide (NaOH) were purchased from FisherScientific (Hampton, N.H.). All chemicals were used as received without further purification. All glassware was cleaned with aqua regia solution, followed by copious rinsing with Nanopure™ $H_2O$ (Barnstead, 18.2 MΩ cm) prior to use.

Instrumentation

Ultraviolet-visible-near infrared (UV-vis-NIR) spectra of Au nanoprisms were collected on a Shimadzu UV-1800 spectrophotometer. The complete Au nanoprism extinction spectrum was obtained by dispersing the sample in $D_2O$ (to avoid interference from $H_2O$ in the NIR) before collection on a Cary-5000 UV-vis-NIR spectrophotometer. Scanning electron microscopy (SEM) analysis of the Au nanoparticles was conducted on an FEI Nova Nano 430 SEM operated at 15 kV at the Nanoscale Research Facility at the University of Florida (UF). Transmission electron microscopy (TEM) samples were prepared by dropping 6 μL of the Au nanoparticle suspension onto a Holey Carbon 400 mesh Cu grid (Ted Pella, Inc.) and allowing the grid to dry in ambient air. TEM analysis was then performed using a JEOL 200CX TEM (located at the Major Analytical Instrumentation Center at UF) operated at 200 kV. Additional high-resolution transmission electron microscopy (HRTEM) images were acquired using a JEOL 2100F HRTEM equipped with a Schottky field-emission gun (FEG) with Cs=1.0 mm operated at 200 kV (located at Brookhaven National Lab, Upton, N.Y.). Annular dark-field scanning transmission electron microscopy (ADF-STEM) imaging was conducted on a Cs-corrected Hitachi HD-27000 equipped with a Cold-FEG operated at 120 kV (located at Brookhaven National Lab, Upton, N.Y.). Images were acquired using a probe convergence semi-angle of 23 mrad, with the inner collection angle of the ADF detector at 53 mrad. Electron energy loss spectroscopy (EELS) data was acquired with a Gatan Enfina spectrometer. The collection angle was approximately 15 mrad while the dwell time was 0.032 s and the spectrometer dispersion was set to 0.05 eV per channel. Energy resolution of the system, as defined by the FWHM and FWTM of the zero loss peak (ZLP), was approximately 0.35 eV and 0.85 eV, respectively. The ZLP was removed using a fitted logarithmic tail model in Gatan Digital Micrograph. The distribution of plasmon modes was plotted by integrating over a 0.1 eV wide window centered on the indicated energy value. Lastly, to account for variation in the EELS signal the intensity of each mode was normalized at each point. This normalization was accomplished by dividing its value by the total intensity of the corresponding EELS spectrum. The thickness of individual Au nanoprisms on the Si substrate was measured using an atomic force microscope (AFM, Asylum Research MFP-3D™) operated in tapping mode (located at the Pacific Northwest National Lab (PNNL) in Richland, Wash.). The 2×2 μm² scan was conducted with a scan rate of 1.0 Hz using the non-contact AFM probes (TETRA15 from K-TEK Nanotechnology). Zeta potential analysis of PVP was conducted at 25° C. on a Zetasizer Nano-ZS (Malvern). Nanoscale secondary ion mass spectrometry (NanoSIMS) multi-element maps were acquired from Au nanoprisms on a Si wafer using a Cameca NanoSIMS 50L (located at PNNL, Richland, Wash.). The as-synthesized nanoparticles were first washed via centrifugation at 5,000 rpm for 5 min and redispersed in Nanopure™ $H_2O$. This procedure was repeated two times to remove excess surfactants from the solution. The cleaned nanoparticles were then deposited onto the Si substrate by drop casting and allowed to dry in a desiccator. A 16.0 keV Cs+ primary ion beam was used to focus a spot size around 50 nm for imaging negative secondary ions. The Cs+ beam was scanned on 6×6 µm² or 8×8 µm² areas to obtain ion images with a definition of 256×256 pixels. The mass spectrometer was fine-tuned to detect $^{12}C^{14}N^-$, $^{127}I^-$, and $^{197}Au^-$ species. For the characterization of Ag nanoprisms, the spectrometer was fine-tuned to detect $^{12}C^{14}N^-$ and $^{107}Ag^-$ species. The secondary ion signals were recorded with electron multipliers. It should be noted that all secondary ion maps were acquired without any pre-sputtering process to specifically collect signals from the top-most surface of the nanostructures. Image processing was carried out using the software ImageJ 1.46r (Wayne Rasband, National Institute of Health, USA, http://rsbweb.nih.gov.ij/index.html) equipped with the OpenMIMS plugin (http://www.nrims.harvard.edu.software.php). To identify the products of methanoloxidation, the reactor headspace gas both before and after 2 h of light irradiation was examined by gas chromatography. The composition of the gas sample (0.2 mL) was detected using a Shimadzu GC-2014 gas chromatograph equipped with a thermal conductivity detector (TCD), with Ar as the carrier gas at a flow rate of 25 mL/min. The reference sample was a mixture containing methanol, formaldehyde, and formic acid. Electrochemical experiments were conducted using a three-electrode electrochemical cell controlled by a potentiostat (EC Epsilon, Bioanalytical Systems, Inc.). The Au nanocrystal photoelectrode served as the working electrode (area of 2 cm²), with a Pt wire auxiliary electrode and a Ag/AgCl reference electrode all immersed in a supporting electrolyte of 0.1 M $NaSO_4$ with 10% (vol.) methanol (tuned to pH 3.0 via HCl addition). All error bars indicate the standard deviation about the mean value obtained from three independent trials.

Synthesis of Au Nanoprisms

Pseudo-spherical Au seeds were prepared according to a previously described method (DuChene, J. S. et al., *Chem. Mater.* 25, 1392-1399 (2013)). A photochemical growth solution was prepared by adding 5 mg of PVP to a mixture of 10 mL Nanopure™ $H_2O$ and 1 mL methanol. Then, 0.8 mL of a 10 mM $HAuCl_4$ aqueous solution and 2 µL of the above-mentioned Au seed solution were added into the growth solution and gently mixed. This represents the standard growth solution used for all experiments unless otherwise indicated. For the growth of triangular Au nanoprisms, 20 µL of 10 mM NaI was also added to this solution. The growth solution was illuminated for 2 h with a halogen lamp (Dolan Jenner, Model No. MI-150) equipped with a bandpass filter (Thor Labs, Inc.) under an incident power of $I_0$~12 mW/cm² on the sample surface. The standard growth protocol involved the use of a 500±10 nm bandpass filter. All photochemical growth experiments were performed under this power ($I_0$~12 mW/cm²) and incident wavelength ($\lambda_{inc}$=500±10 nm) unless otherwise stated. For wavelength-dependent growth experiments, the solution was illuminated with various bandpass filters from $\lambda_{inc}$=480-660 nm, each exhibiting a bandwidth (FWHM) of 10±2 nm. Nanostructure growth products were collected after synthesis by centrifugation at 5,000 rpm for 5 min and redispersed in Nanopure™ $H_2O$. This procedure was repeated two more times to remove excess surfactants from the nanostructure surface before characterization of the samples by electron microscopy.

Single-Nanoparticle Growth Experiments Conducted on a Si Substrate

Smaller Au nanoprisms and Au nanospheres were obtained using the above-described synthetic method with a shorter irradiation time of 30 min. After the reaction these products were centrifuged and washed with Nanopure™ $H_2O$ three times, as described above. The nanostructures were then immobilized on the Si substrate by drop-casting a small aliquot onto the substrate and allowing it to thoroughly dry in a desiccator. The substrate was then immersed in a fresh growth solution (as prepared above) to conduct further experiments under dark or light conditions. All Si substrates were marked to provide a means of inspecting an individual nanocrystal before growth commenced and then relocating the same nanostructure after the reaction was ceased. This approach enabled the observation of the growth trajectories of individual Au nanoparticles. For comparison with the hot spot distribution observed from the EELS maps, the samples were illuminated ($I_0$~12 mW/cm²) for 30 min with a halogen lamp (Dolan Jenner, Model No. MI-150) equipped with a bandpass filter (Thor Labs, Inc.) under the following incident wavelengths: $\lambda_{inc}$=520±10 nm (~2.4 eV), $\lambda_{inc}$=780±10 nm (~1.6 eV), or $\lambda_{inc}$=960±10 nm (~1.3 eV).

Electrochemistry

Electrochemical experiments were conducted via the construction of a three-electrode electrochemical cell controlled by a potentiostat (EC Epsilon, Bioanalytical Systems, Inc.) with a Au nanocrystal photoelectrode (working), a Pt wire auxiliary electrode, and a Ag/AgCl reference electrode all immersed in a supporting electrolyte of 0.1 M $NaSO_4$ with 10% (vol %) methanol (tuned to pH 3.0 via HCl addition to mimic the growth solution pH conditions). The Au nanocrystal photoelectrodes were prepared as follows: Au nanoparticles without PVP were first obtained via UV-light irradiation ($\lambda_{inc}$=280-400 nm) of an aqueous $HAuCl_4$ solution to photochemically reduce this metal precursor directly into Au nanoparticles in the absence of any surfactants. These Au nanoparticles were then deposited onto the fluorine-doped tin oxide (FTO) glass substrate by drop-casting and subsequent heating at 150° C. for 20 min to ensure sufficient adhesion with the underlying substrate. The working electrode area was 2 cm². The photoanode was illuminated through the FTO glass substrate with an ozone-free 300 W Xe lamp (Newport Corp.) equipped with a 495 nm longpass filter (Newport Corp.) under an incident power of $I_0$~1.5 W/cm². To modify the nanocrystals with PVP, the exact same Au nanoparticle electrode was then dipped into an aqueous solution containing 5 mg/mL PVP for 10 min to allow PVP adsorption. The Au nanoparticle electrode (now functionalized with PVP molecules) was then copiously rinsed with Nanopure™ $H_2O$ to remove any molecules not specifically bound to the Au nanoparticles. The photoelectrode was then illuminated under identical conditions as before to provide a direct comparison of the photovoltage obtained from the exact same Au nanoparticle electrode with and without PVP. For the photovoltage comparison between planar-twinned Au nanoprisms and multiply-twinned Au nanoparticles, the concentration of Au nanomaterials in each solution was first determined by ICP-MS (Perkin Elmer, Optima 3200RL). Then, the relative concentration was adjusted to ~63 mg/mL, and 100 µL of Au nanomaterials were deposited on the electrode surface, which was further treated as described above.

Plasmon-Driven Synthesis of Au Nanoprisms

In this contribution, we expand the realm of noble metal nanostructures accessible via plasmonic photochemistry with the demonstration of plasmon-driven Au nanoprism synthesis. Growth studies at the single-nanoparticle level elucidate the mechanics of the plasmon-driven process and unambiguously clarify the anisotropic growth mechanism. Nanoscale secondary ion mass spectrometry (NanoSIMS)

was employed to probe the physical location of the surfactant polyvinylpyrrolidone (PVP) on individual Au nanostructures at the molecular level, revealing that it preferentially adsorbs onto twin-plane defects along the nanoprism perimeter instead of the top {111} facets as previously suggested. Electrochemical studies on Au nanocrystal electrodes further demonstrate that adsorbed PVP facilitates the accumulation of hot electrons upon optical excitation, indicating that this surfactant performs a unique function as a photochemical relay to enable the anisotropic growth of Au nanoprisms from spherical Au seeds. These findings assign a new role to this ubiquitous surfactant that is distinct from its widely recognized function as a crystal-face-blocking ligand in nanomaterials synthesis. Further investigation showed that nanocrystal twinning itself regulates the transport of hot electrons under plasmon excitation, thereby modulating the photochemical growth kinetics of Au nanocrystals based upon their intrinsic structural differences. These mechanistic insights inspired the development of a simple method for selectively producing hexagonal or triangular Au nanoprisms in high yield (~90%), demonstrating the general utility of plasmonic photochemistry for manipulating the growth of noble metal nanocrystals.

Figures 9A, 9B, 9C, 9D, 9E, 9F, 9G:
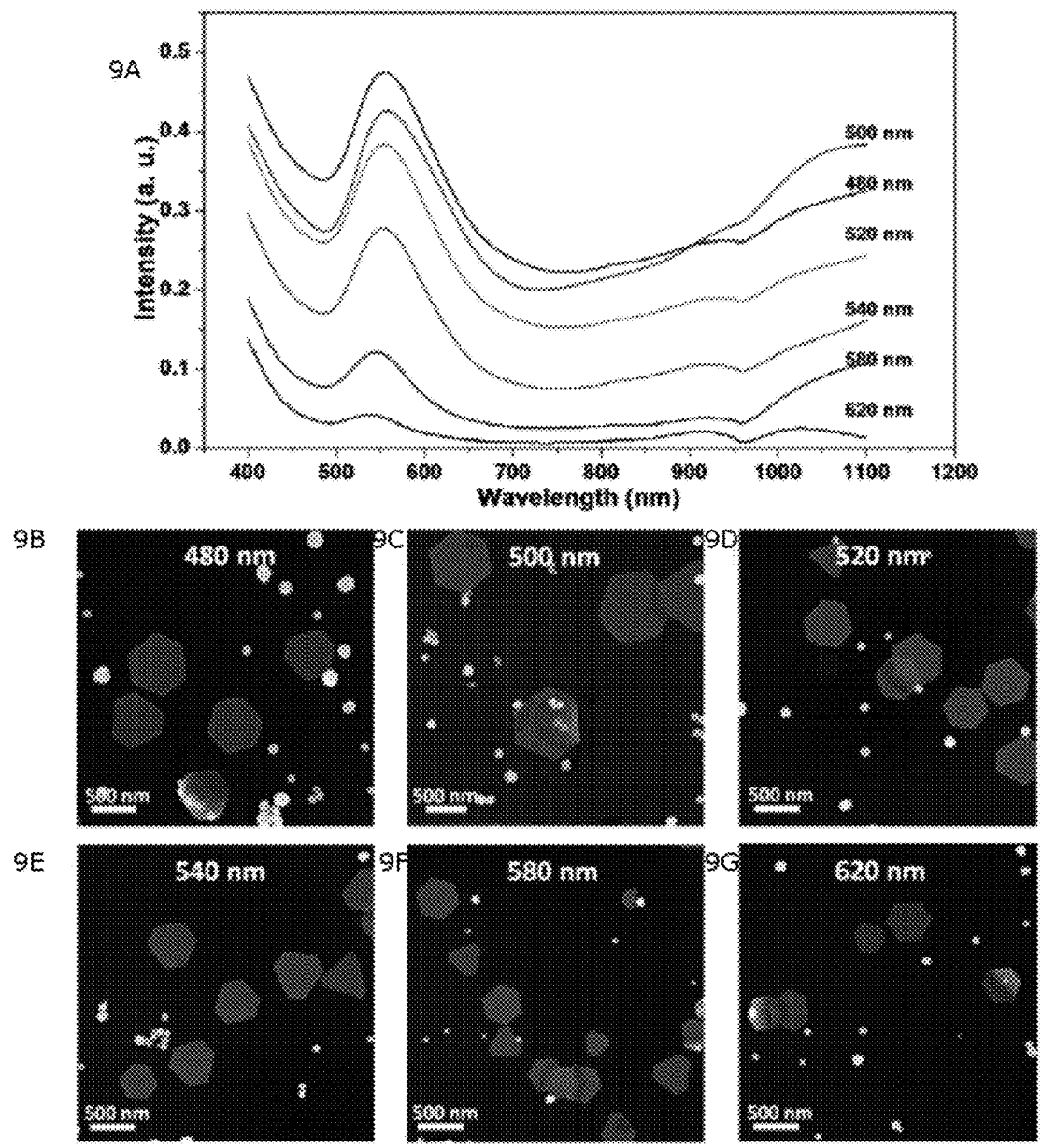
FIGS. 9A-9G demonstrate the influence of incident excitation wavelength on Au nanostructure growth.

Pseudo-spherical Au nanoparticles with an average size of ca. 7±3 nm (FIG. 1A) were used as seeds for the plasmon-driven growth of anisotropic Au nanoprisms (see Methods). The photochemical reaction was initiated by irradiating an aqueous growth solution containing the Au seeds, tetrachloroauric acid ($HAuCl_4$), PVP, and methanol with $\lambda_{inc}$=500±10 nm light to ensure that the incident excitation wavelength ($\lambda_{inc}$) was commensurate with the SPR of the Au seeds (FIG. 1B, black curve). Scanning electron microscopy (SEM) revealed that a mixture of Au nanoprisms and Au nanospheres were produced after 2 h of irradiation (FIG. 1C). The nanoprisms exhibit either triangular or hexagonal morphologies predominantly enclosed by {111} facets with an average edge length (l) of 496±68 nm and an average thickness (h) of 22.0±0.4 nm (FIGS. 5A-5D). The average diameter (d) of the Au nanospheres was 105±14 nm. The photochemical growth process was monitored spectroscopically over the course of the 2 h reaction and correlated with the structural evolution of these Au nanocrystals via electron microscopy (FIGS. 6A-6M). The extinction spectra displayed the simultaneous emergence of two distinctive SPR features indicative of the concurrent growth of both pseudo-spherical nanoparticles ($\lambda$~550 nm) and nanoprisms ($\lambda$~1100 nm). Periodic inspection of the nanocrystal morphology by SEM demonstrates that both nanostructures evolve independently over the 2 h reaction (FIGS. 6A-6M and FIG. 7). The simultaneous emergence and continued growth of both SPR features demonstrates that both nanospheres and nanoprisms grow independently of each other; that is, they evolve from different initial seed structures into larger pseudo-spherical nanoparticles or hexagonal nanoprisms. The independent growth of both Au nanospheres and nanoprisms is also demonstrated by periodic inspection of these Au nanostructures over the course of the 2 h reaction by SEM (FIGS. 6B-6E) along with the corresponding size distribution histograms for both nanospheres (FIGS. 6F-6I, red) and nanoprisms (FIGS. 6J-6M, blue). Both nanostructures simultaneously increase in size over the course of the 2 h reaction. It must be emphasized that this result indicates that there is no interconversion of these larger (~20-100 nm) spherical Au nanoparticles into hexagonal Au nanoprisms, as has previously been observed in the plasmon-mediated growth of Ag nanostructures. This difference is due to the greater chemical stability of Au compared to Ag15, since Au seeds are not readily susceptible to photo-oxidation during plasmon excitation like Ag seeds. We emphasize this difference between the Au and Ag systems to clarify the distinction in growth mechanisms between these otherwise very similar noble metal systems. As such, the Au precursors are supplied by $AuCl_4^-$ species in the growth solution, rather than from the sacrificial oxidation of unstable Au seeds. It is also noted that the yield of nanoprisms ~21% is roughly consistent with the percentage of planar-twinned nanocrystals present in the initial seed solution (~30%), implicating a seed-mediated growth process. Taken together, these data prove that all the Au nanocrystals grow under visible light, and that only those with the proper crystal structure evolve into the nanoprisms. The multiply-twinned nanocrystals, on the other hand, continually increase in size without developing anisotropy, as evidenced by the fact that the feature $\lambda$max~550 nm continually increases in amplitude while exhibiting a slight red-shift in its spectroscopic position. The nanoprisms (both triangular and hexagonal) were obtained with ca. 21% yield (by shape), consistent with the percentage of planar-twinned nanocrystals observed in the seed solution (FIGS. 8A-8D). Such a correlation confirms that nanoprism growth proceeds via a seed-mediated pathway. Further investigation of the growth process shows that the reduction of $HAuCl_4$ increased linearly with the incident light intensity (FIG. 1D): this relationship is indicative of a photochemical reaction driven by visible light. A series of bandpass filters were then used to examine the influence of the incident light wavelength ($\lambda_{inc}$) on the reduction of Au precursors ($HAuCl_4$). As shown in FIG. 1B (red points) and FIGS. 9A-9G, the visible-light-driven production of Au nanostructures was directly correlated with the optical properties of the Au seeds. As shown in the SEM images, Au nanospheres and Au nanoprisms were produced regardless of the incident wavelength ($\lambda_{inc}$), only the relative size and total number density of Au nanocrystals changed. For instance, the average edge length of Au nanoprisms obtained after 2 h of irradiation with 500 nm light was ca. 496 nm (FIG. 9C) while under 620 nm light the nanoprism edge length only reached ca. 260 nm (FIG. 9G). Further quantification of the amount of Au precursors ($HAuCl_4$) left in the growth solution by UV-Vis spectroscopy after the 2 h reaction further correlates the reduction of Au precursors in the growth solution (FIG. 1B, red points) with the plasmon resonance of the Au nanocrystals (FIG. 1B, black curve). Taken together, these results demonstrate that the incident excitation wavelength directly determines the total consumption of Au precursors in the growth solution over the course of the reaction and therefore affects the final size of the Au nanostructures produced. These data confirm that SPR excitation of the Au nanocrystals is required to initiate the photochemical reaction.

We examined the Au system by using annular dark-field scanning transmission electron microscopy (ADF-STEM) in tandem with electron energy loss spectroscopy (EELS) to map the spatial distribution of plasmon modes on a single Au hexagonal nanoprism (FIGS. 2A-2E) and a single Au triangular nanoprism (FIG. 2F-2J). These EELS maps depict the spatial variation of distinct plasmon modes along the nanoprisms, as the hot spots clearly shift from the center of the nanoprisms (~2.4 eV) to their perimeter (~1.3 eV) with decreasing energy (compare FIG. 2B to FIG. 2E). The influence of these hot spots on the nanostructure growth process was then investigated by monitoring the growth of individual nanoprisms immobilized on a silicon (Si) substrate while hot spots on different positions of these nanostructures were selectively excited with specific irradiation wavelengths ($\lambda_{inc}$=520 nm, 780 nm, 960 nm). These wavelengths were chosen to coincide with the optically accessible (i.e. bright) plasmon modes of the Au nanoprisms observable from the extinction spectrum. Despite the anisotropic distribution of these different hot spots on the nanoprisms (FIG. 2A-2J), significant growth occurred only along the nanoprism perimeter (FIG. 2K-2P). Our finding is consistent with previous growth studies on Ag nanoparticles: isotropic nanocrystal growth was consistently observed despite manipulating the spatial orientation of the plasmonic hot spots by varying the incident light polarization. This discrepancy between the near-field distribution and the nanoprism growth direction demonstrates that the anisotropic morphology is not determined by the spatial distribution of these plasmonic hot spots.

Figure 10:
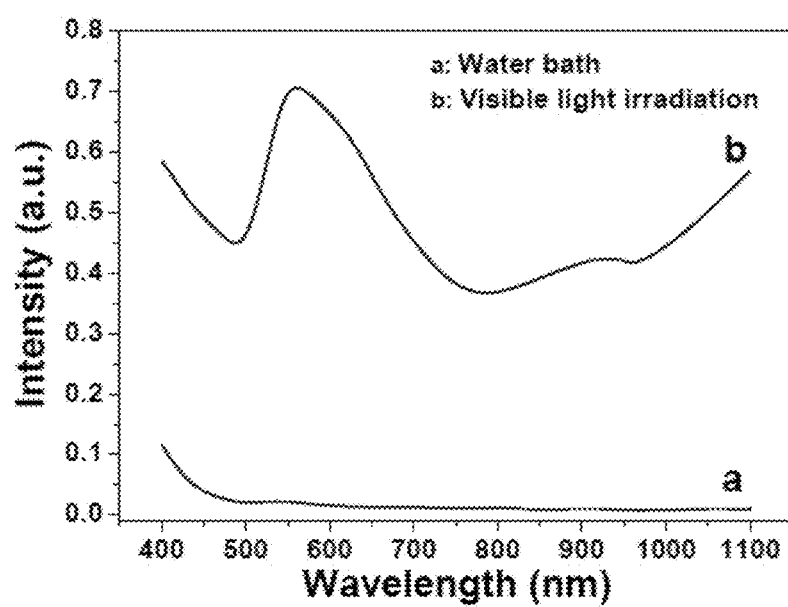
FIG. 10 is a graph from a photothermal control experiment conducted in the dark at 32° C. for 2 h plotting the extinction spectra of (a) the growth solution after 2 h of incubation in the dark while immersed in a water bath maintained at 32° C. and, for comparison, (b) the extinction spectra of the growth solution after irradiation with 500±10 nm light for 2 h.

Although the possibility of local photothermal heating must be considered in a plasmon-driven reaction, the excellent thermal conductivity of Au ensures that an isotropic temperature distribution is rapidly (~ps-ns) established on the entire nanoparticle surface. This thermal uniformity renders such a process incapable of promoting the anisotropic growth of nanoprisms. Since the bulk solution temperature measured under low-power continuous light irradiation (32° C. after 2 h) can be used as a surrogate for the nanoparticle surface temperature, the growth solution was incubated at 32° C. in the dark for 2 h to assess any photothermal contribution; however, no detectable growth was observed (FIG. 10). The hot electrons produced during plasmon decay quickly equilibrate with the metal lattice via electron-phonon coupling (~1 ps), thereby elevating the surface temperature of the metal nanoparticles. Since the heat transfer from a plasmonic-metal nanoparticle to the surrounding solution is ultrafast (~1 ns), the bulk solution temperature (32° C. measured after 2 h) can be used as a surrogate for the nanoparticle surface temperature under low-power visible-light irradiation. The growth solution was therefore incubated at 32° C. in the dark for 2 h; however, no noticeable SPR features were observed via UV-Vis spectroscopy (a in FIG. 10), indicating that no Au nanoparticle growth ensued. This result shows that the bulk solution temperature observed under visible-light irradiation is not high enough to enable PVP to directly reduce the $HAuCl_4$ precursors, and confirms a negligible contribution from photothermal heating to the plasmon-driven growth of Au nanostructures. It is further noted that the linear relationship observed between the plasmon-driven reduction of $HAuCl_4$ and the incident light intensity (FIG. 1D) is the signature of an electron-driven photochemical reaction, rather than a photothermal process.

Figures 11A, 11B, 11C:
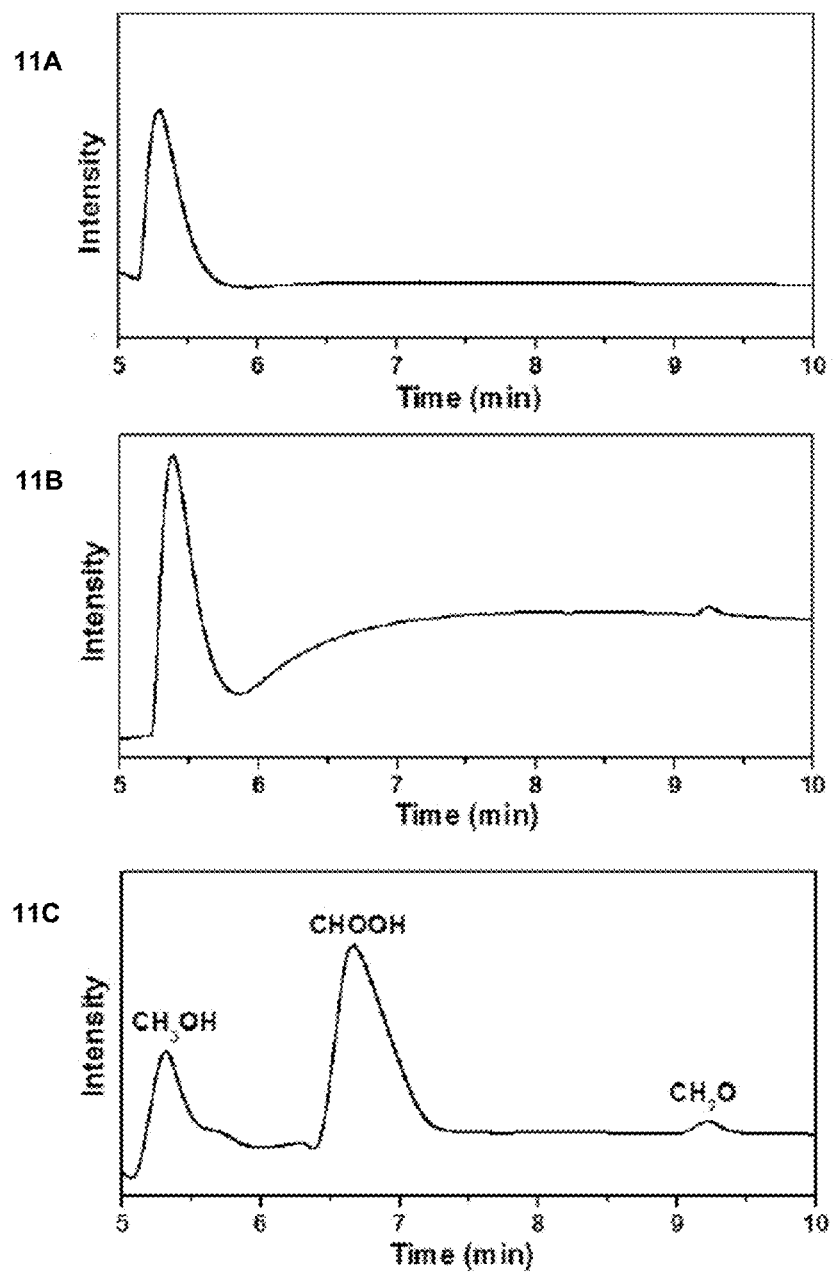
FIGS. 11A-11C demonstrate the detection of the methanol oxidation product using gas chromatography.
Figures 12A, 12B, 12C, 12D:
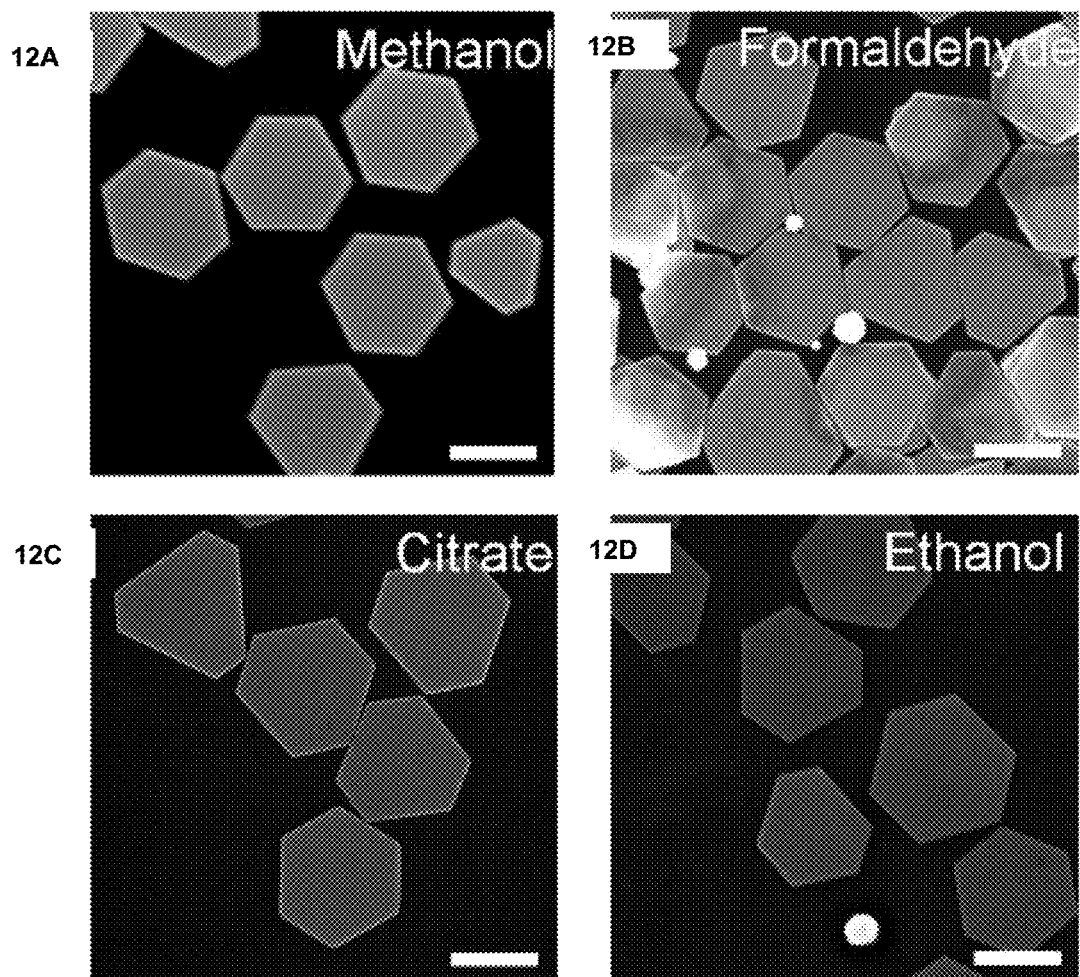
FIG. 12A-12D demonstrate the synthesis of Au nanoprisms using various hole scavengers.
Figures 13A, 13B, 13C:
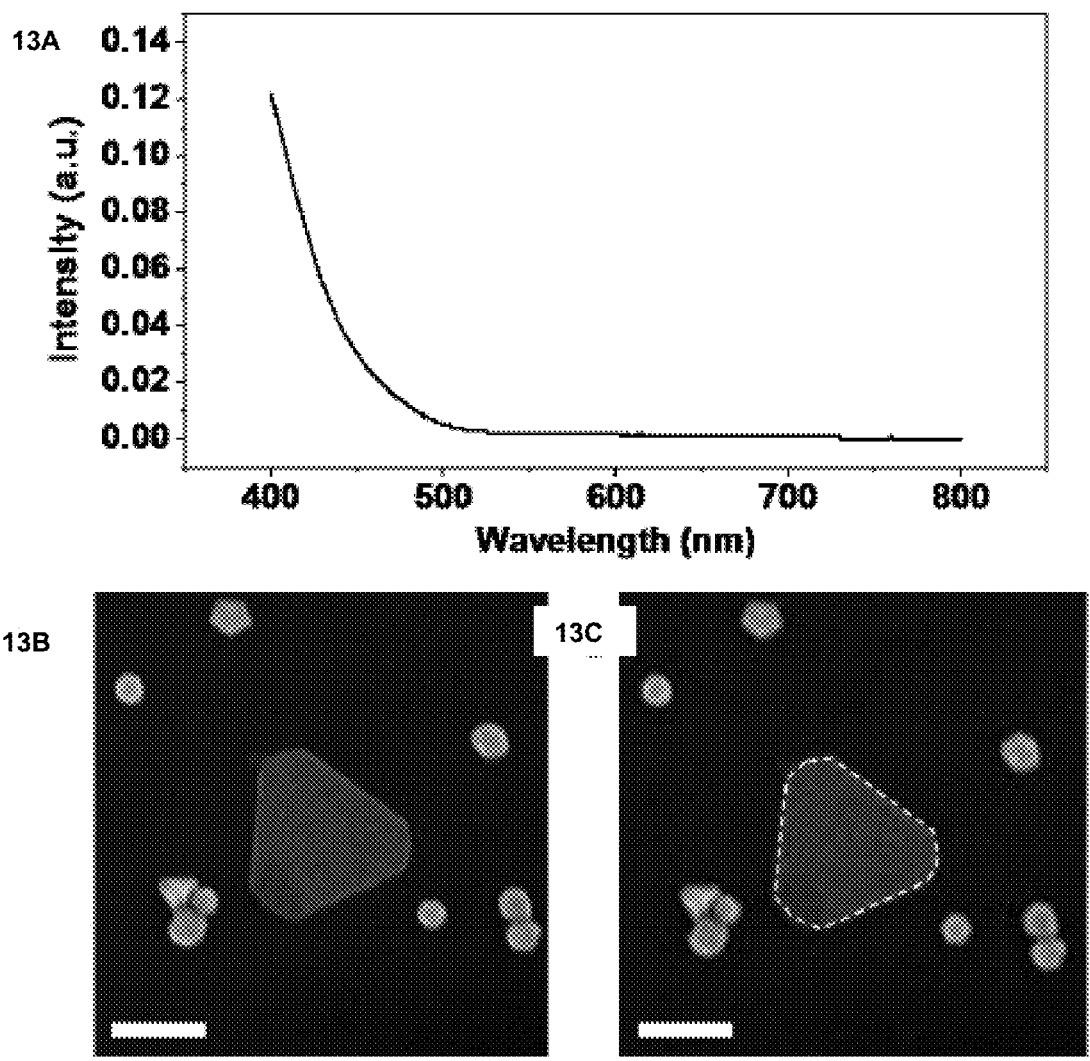
FIGS. 13A-13C demonstrate the control experiments without methanol in the photochemical growth solution.
Figure 14:
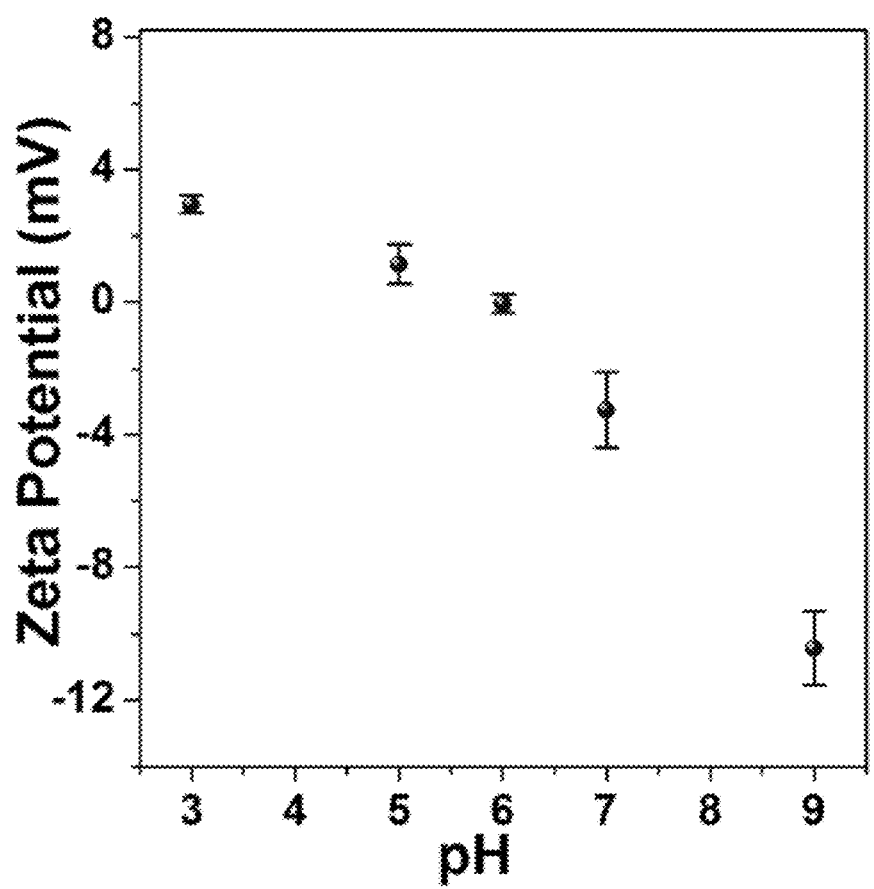
FIG. 14 is a graph of the zeta potential measurement of PVP as a function of solution pH.
Figures 15A, 15B, 15C, 15D, 15E:
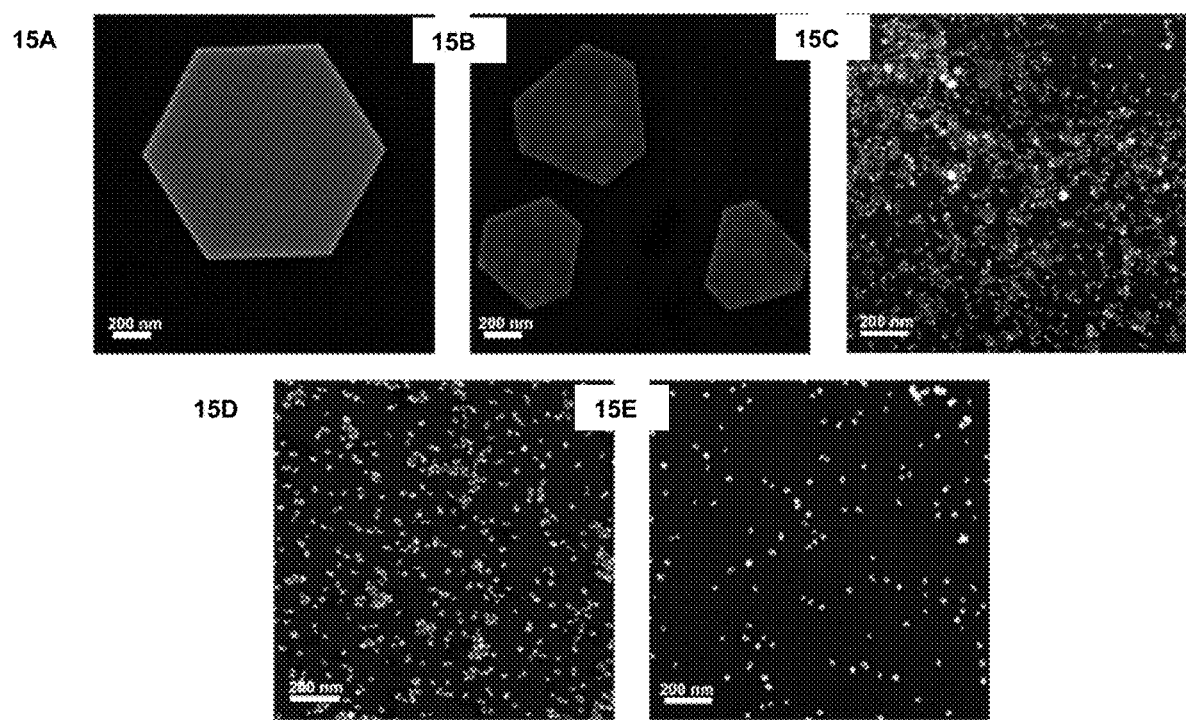
FIGS. 15A-15E demonstrate the influence of growth solution pH on Au nanoprism synthesis. SEM images of Au nanostructures obtained in the growth solution with different pH values.
Figure 16:
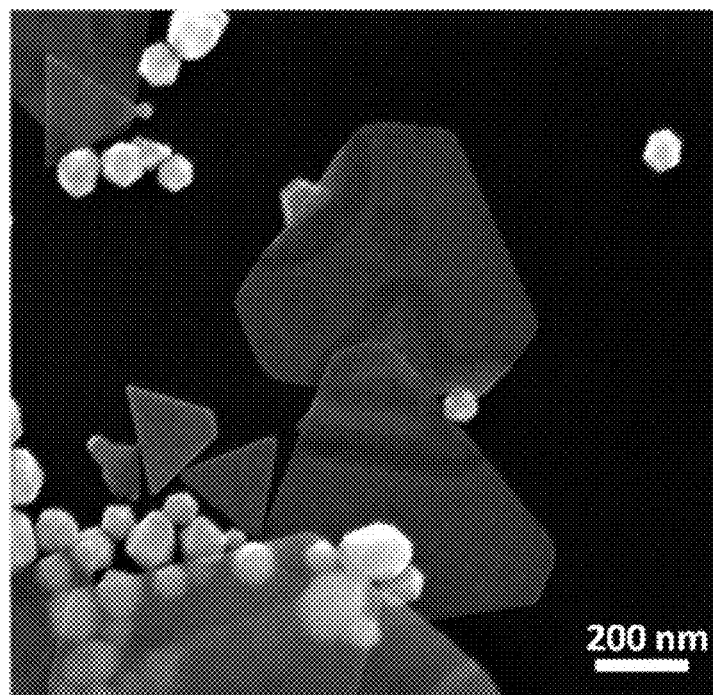
FIG. 16 demonstrates an SEM images from a control experiment with PVP monomer in the growth solution.

Taken together, these observations strongly suggest that the plasmon-mediated production of hot electron-hole pairs drives the photochemistry necessary for nanostructure growth. The hot holes should be quickly scavenged by the sacrificial reagent methanol, which is irreversibly oxidized to yield formaldehyde as a photochemical byproduct (FIGS. 11A-11C). Hot electrons then relax to the metal Fermi level and reduce Au precursors from solution to enable plasmon-driven growth. However, it is unlikely that these electrons can directly reduce the Au precursors due to the incommensurate timescales between the hot electron lifetime (~fs-ps)[8,28] and the slow kinetics of $HAuCl_4$ reduction (~μs-ms)[29]. This plasmon-driven photocatalytic model therefore requires an intervening chemical species adsorbed on the Au nanoparticle surface that can prolong their lifetime and foster the multi-electron reduction of $HAuCl_4$. A cursory examination of our growth solution composition implies that the surfactant PVP is the only constituent capable of performing the aforementioned function (FIGS. 12A-12D). It must be noted that PVP itself is incapable of directly reducing the Au precursor under our experimental conditions (FIGS. 13A-13C). Further experiments show that the surface charge of PVP is dependent upon solution pH (FIG. 14) and that Au nanoprisms were only observed when a positive surface charge was imparted to PVP by the acidic (pH 3) growth solution (FIGS. 15A-15E). A positive surface charge is observed for PVP under acidic conditions (pH 3.0 and pH 5.0), while a negative charge was observed under neutral and alkaline conditions (pH7.0 and pH 9.0). It is noted that around pH 6.0 there was hardly any surface charge detected for PVP. These data demonstrate that the surface charge of PVP is dependent upon the solution pH. It is also noted that Au nanoprisms grow if the PVP monomer (N-methyl-2-pyrrolidone) is substituted for the polymer (FIG. 16), indicating that the γ-lactam ring comprises the critical chemical moiety in PVP that enables anisotropic growth. SEM image showing Au nanoprisms are also produced if the PVP is replaced with its monomer: N-methyl-2-pyrrolidone. This result illustrates that the γ-lactam ring constitutes the critical chemical moiety in the PVP surfactant that facilitates anisotropic growth during the plasmon-driven reaction.

These results illustrate that the pH of the growth solution can impact the formation of Au nanoprisms. Under these conditions, the Au nanoprisms were only observed at pH 3.0 and pH 5.0, when a positive surface charge was imparted to PVP by the acidic growth solution (see FIG. 14). Furthermore, the growth rate at pH 3.0 is higher than that at pH 5.0 based on the significant difference in Au nanoprism size [compare images (FIG. 15A) and (FIG. 15B)]. With increasingly alkaline conditions (pH 6.0, 7.0, and 9.0), the Au seeds (ca. 7 nm) only marginally increased in size (ca. 20 nm) over the 2 h reaction. These results demonstrate that the positive surface charge of PVP plays an important role in promoting nanoparticle growth, and implies that PVP forms an electrical adlayer on the Au nanocrystal capable of coulombically stabilizing hot electrons generated via SPR excitation to facilitate the reduction of Au precursors on the nanocrystal surface. All these results suggest that PVP could fulfill a complementary role in the plasmon-driven process: the electrostatic force from positively-charged PVP molecules would induce the formation of an electrical adlayer on the Au nanocrystal surface capable of stabilizing hot electrons generated via plasmon excitation. Additionally, this positively-charged adlayer should permit PVP molecules to capture negatively-charged Au precursors ($AuCl_4^-$) from solution and form a PVP-metal complex for facilitating reduction reactions on the Au nanostructure surface[30].

Figure 17:
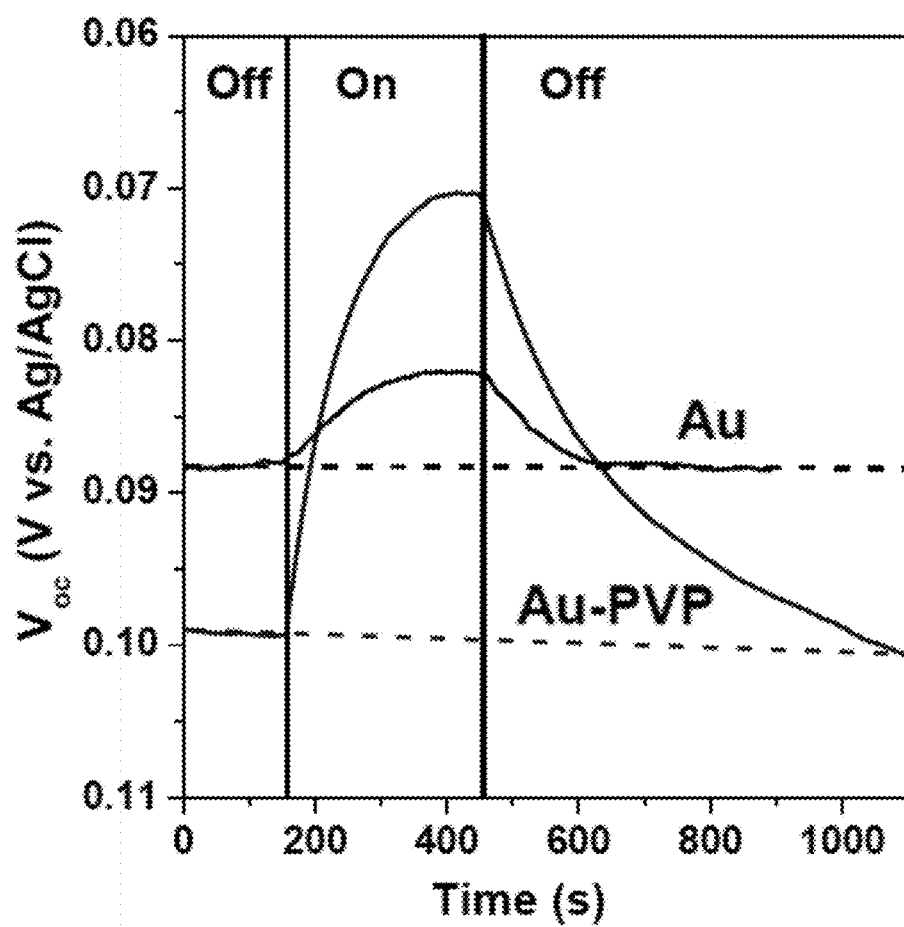
FIG. 17 is a graph of the transient open-circuit voltage [$V_{oc}(t)$] rise/decay from the same Au nanoparticle photoelectrode with (as indicated, "Au-PVP") and without (as indicated, "Au") the modification of PVP during excitation/termination of visible-light irradiation ($\lambda_{inc}$>495 nm). Horizontal dashed lines represent the open-circuit voltage (Voc) baselines obtained under dark conditions.

Electrochemical evidence for the direct involvement of PVP in the plasmon-driven growth of Au nanoprisms was obtained by monitoring the open-circuit voltage ($V_{oc}$) of Au nanocrystal electrodes under visible-light irradiation (see Methods). As the photovoltage ($V_{ph}=V_{oc,\ light}-V_{oc,\ dark}$) established under steady-state conditions corresponds to the accumulation of hot electrons within the Au nanocrystals, chronopotentiometry[10,31] was used to assess the ability for adsorbed PVP molecules to participate in plasmon-driven photochemistry. Upon exposure to visible-light irradiation ($\lambda_{inc}$>495 nm), a prompt rise in photovoltage ($V_{ph}$~28 mV) was observed from the Au nanoparticles functionalized with PVP, while only a modest photovoltage ($V_{ph}$~6 mV) was established in the absence of this surfactant (FIG. 17).

The photovoltage [Vph=Voc(light)−Voc(dark)] established within the photoelectrode during irradiation corresponds to the displacement of the Fermi level (EF) of the Au nanocrystals from their ground state in the dark [EF(dark)] to an excited state under light irradiation [EF(light)] with respect to the redox couple in solution[where EF(redox)=EF (dark)]. The production of hot electrons within the Au nanocrystals during optical excitation can therefore be probed electrochemically via monitoring the open-circuit voltage (Voc) of the photoelectrode, since the Voc shifts to more negative potentials as electrons accumulate within the plasmonic-metal nanostructures. Au nanocrystals were specially prepared in the absence of any surfactants to enable an unambiguous determination of the role of PVP in stabilizing hot electrons within the metal nanocrystals (see Electrochemistry section in Methods for experimental details). Only a modest photovoltage ($V_{ph}$~6 mV) was established in the bare nanoparticle electrode without any PVP molecules (black curve). This same nanoparticle electrode was then modified with PVP (see "Electrochemistry" section). After surface modification with PVP, a shift in the rest potential (~11 mV) of the Au nanoparticle electrode was observed to more positive potentials (blue curve). This positive shift in $V_{oc}$ under dark conditions is indicative of a lower Fermi level, suggesting charge redistribution from the Au nanocrystals to adsorbed PVP molecules. Upon photoexcitation of the Au nanocrystals, a prompt shift in $V_{oc}$ was observed to more negative potentials and a significant photovoltage ($V_{ph}$~27 mV) was established within the Au nanocrystals modified with PVP (blue curve). These results indicate that PVP molecules assist with the accumulation of SPR-generated electrons on longer time scales to establish a significant photovoltage on the Au nanocrystal surface under visible-light irradiation. These results demonstrate that adsorbed PVP molecules assist with the accumulation of hot electrons on the Au nanocrystals over longer timescales to enable the reduction of Au precursors.

Figures 3A, 3B, 3C, 3D, 3E:
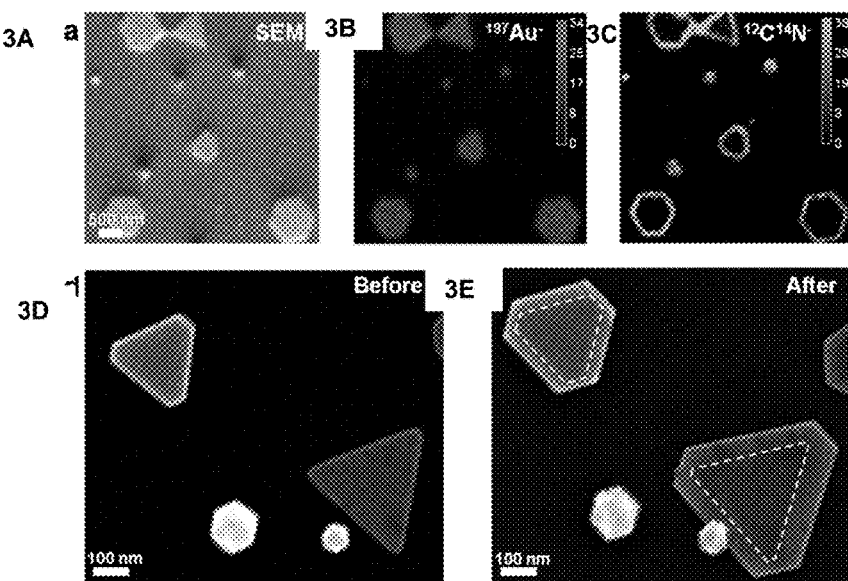
FIGS. 3A-3E demonstrate the role of PVP in directing the anisotropic growth of Au nanoprisms.
Figure 18:
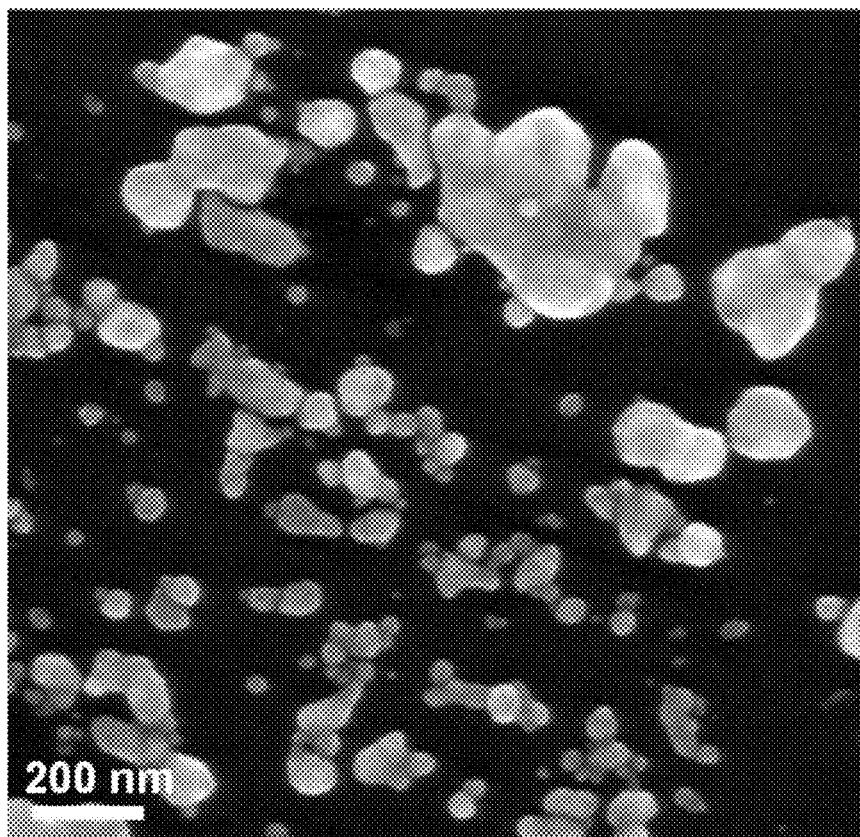
FIG. 18 is an SEM image showing only large aggregates and irregularly shaped nanoparticles are produced if the standard growth solution is irradiated for 2 h with 500±10 nm light without PVP. This result illustrates the importance of PVP in facilitating anisotropic growth during the plasmon-driven reaction.

This proposed function for PVP implies that the physical location of this surfactant should play a critical role in determining the anisotropic growth of the Au nanoprisms. Accordingly, NanoSIMS was used to probe the spatial distribution of PVP molecules on individual Au nanoprisms (FIGS. 3A-3C). As shown in FIG. 3C, $^{12}C^{14}N^-$ signals attributable to adsorbed PVP molecules were primarily detected from the perimeters of the nanoprisms rather than their top {111} facets, while $^{12}C^{14}N^-$ signals were observed from the entire surface of the pseudo-spherical nanoparticles. This discovery is striking, as it shows that PVP is serving a distinct function from its widely accepted role as a crystal-face-blocking ligand in shape-controlled nanomaterials synthesis. Instead, these NanoSIMS results reinforce our proposed role for PVP as an electrochemical relay. The adsorption of positively-charged PVP molecules constitutes an electrical adlayer along the Au nanoprism perimeter. After hot holes are quickly scavenged by methanol, this formed PVP-Au interface coulombically stabilizes the hot electrons produced via optical excitation on a longer timescale to build up a photovoltage on the nanoprism (Supplementary FIG. 13). Meanwhile, the positively-charged electrical adlayer also interacts with negatively-charged Au precursors ($AuCl_4^-$) in solution to form a surfactant-metal precursor complex[30] along the nanoprism perimeter. Thus, these two functions cooperatively couple hot electrons with Au precursors to preferentially promote lateral growth and facilitate the formation of anisotropic Au nanoprisms (FIG. 1C). It is noted that only irregularly shaped Au nanostructures were obtained when PVP was excluded from the growth solution (FIG. 18), demonstrating that this surfactant performs an integral function in regulating the structural evolution of anisotropic Au nanoprisms from isotropic Au seeds.

Figures 19A, 19B, 19C, 19D:
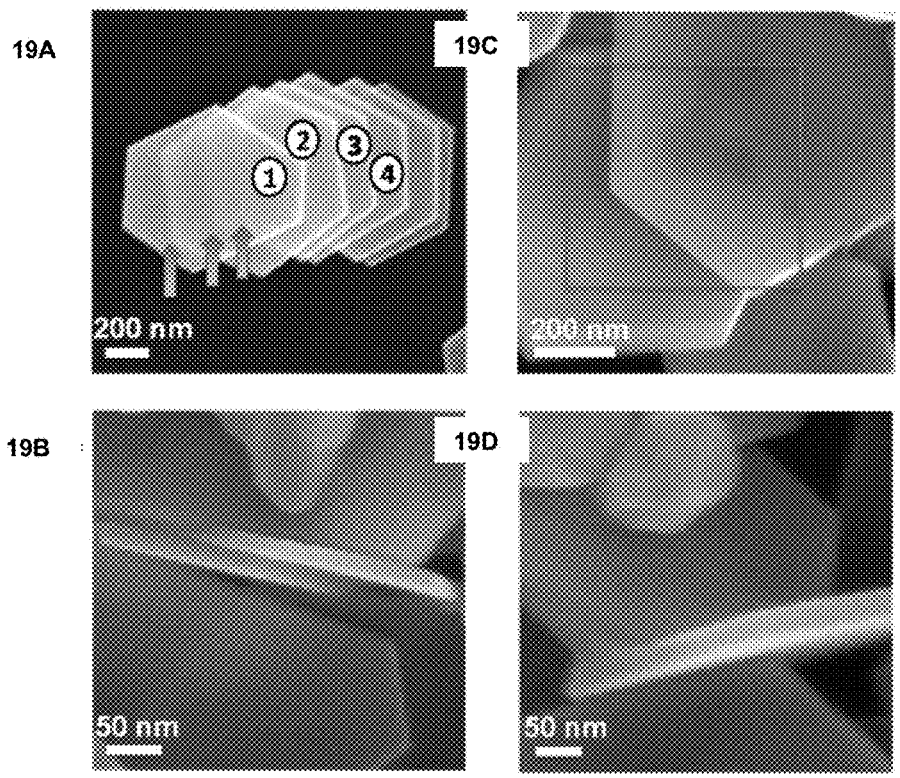
FIGS. 19A-19D demonstrate the influence of PVP concentration on the thickness of Au nanoprisms.
Figures 20A, 20B, 20C:
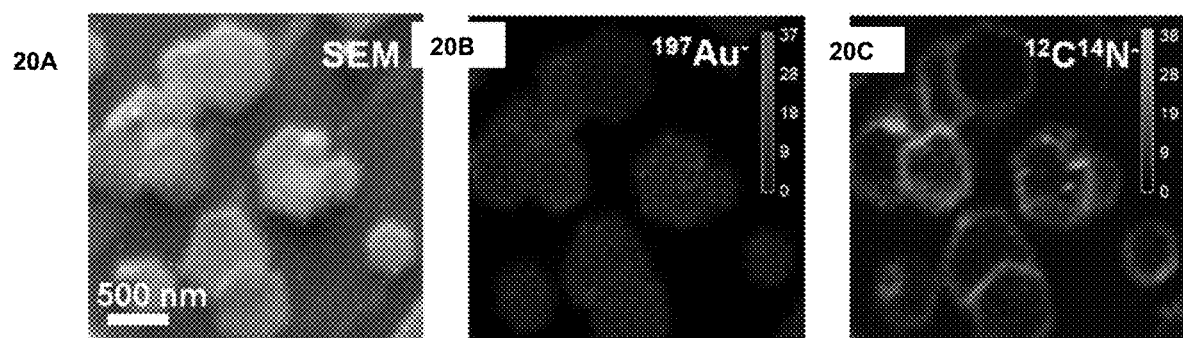
FIGS. 20A-20C demonstrate NanoSIMS data of Au nanoprisms produced using high quantities of PVP.
Figure 21A:
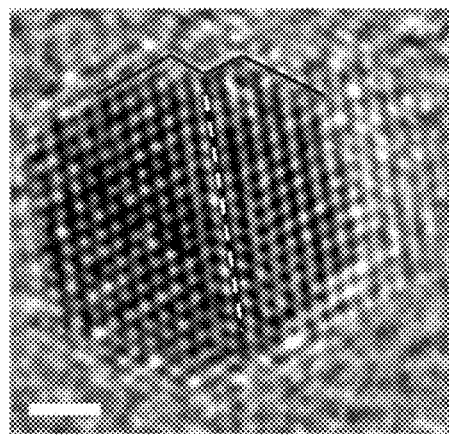
FIGS. 21A-21D demonstrate the identification of defects near twin boundaries on Au nanocrystals.
Figure 21B:
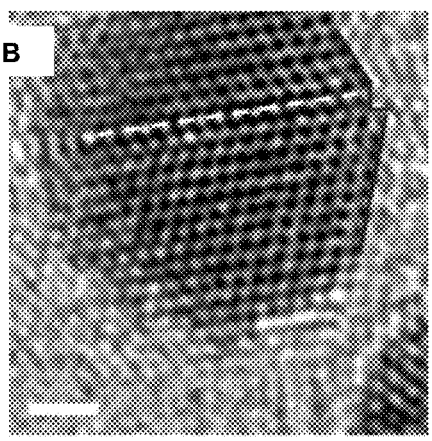
Figure 21C:
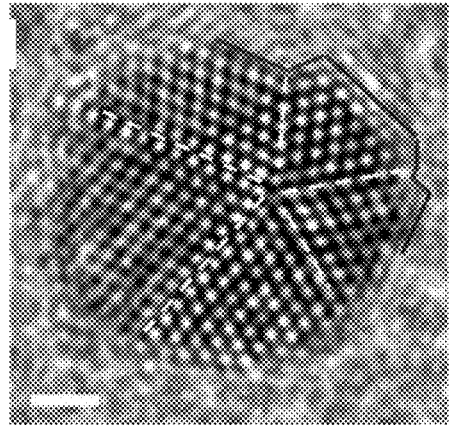
Figure 21D:
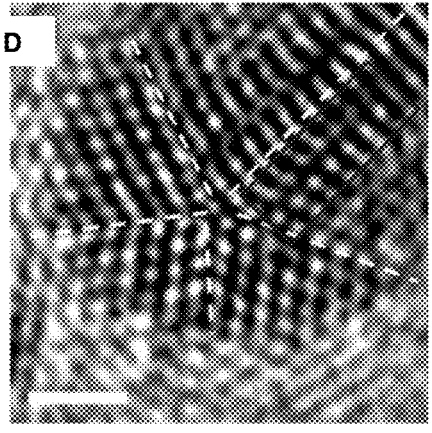
Figures 22A, 22B, 22C, 22D, 22E, 22F:
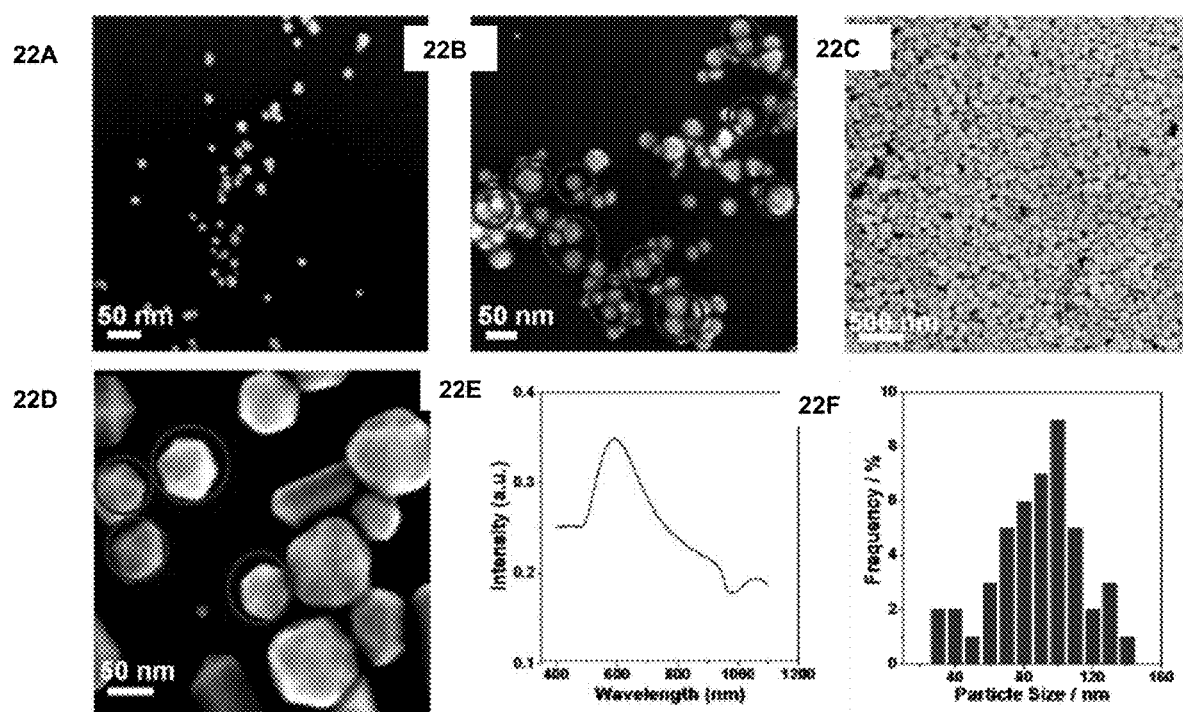
FIGS. 22A-22F demonstrate Au nanoparticles obtained from various incubation periods in the dark.
Figures 23A, 23B, 23C, 23D:
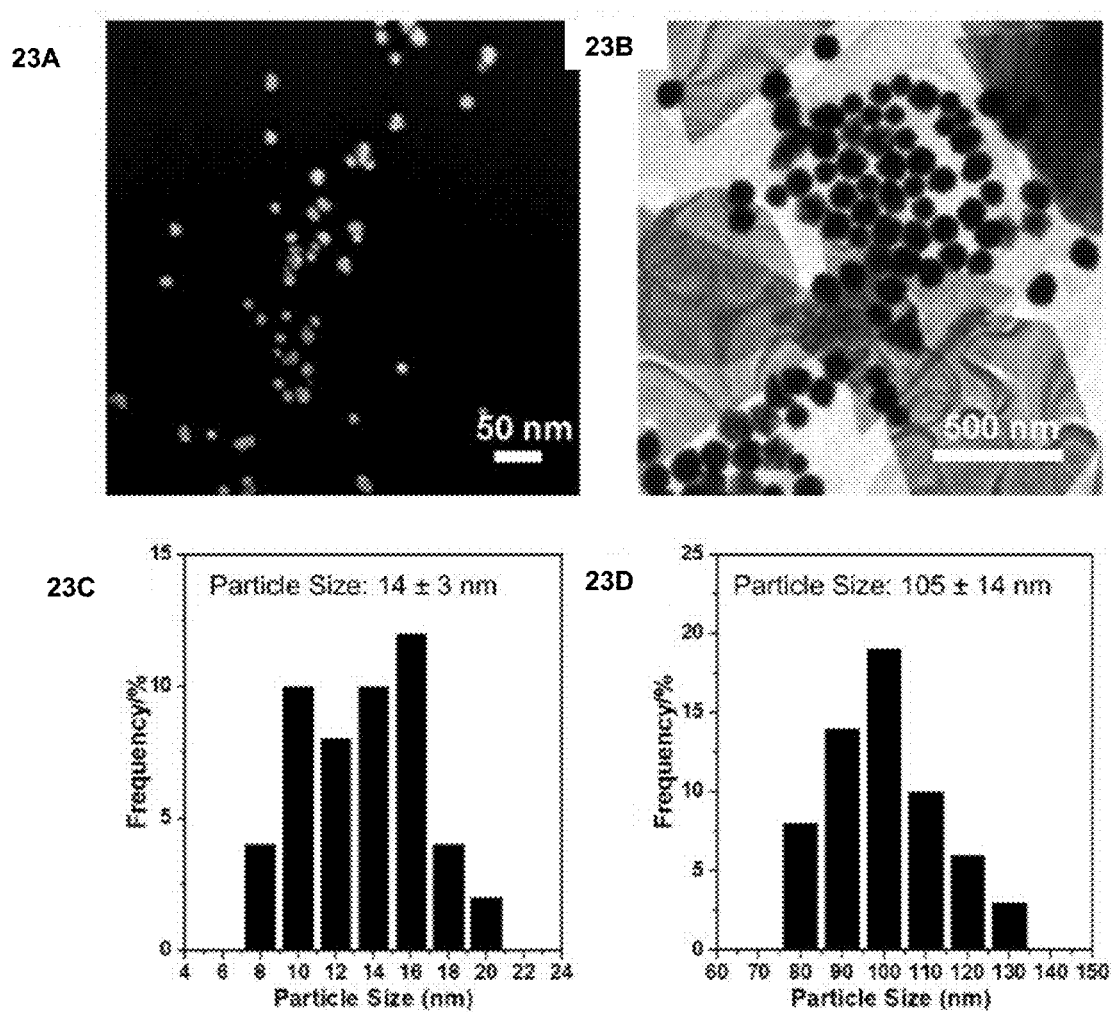
FIGS. 23A-23D depict a comparison of the Au nanoparticle growth rates in light and dark conditions. The growth rate was calculated by assuming a perfect spherical shape for the nanoparticles and using the average radius of the Au nanoparticles. The nanoparticles were counted from a suite of SEM images (FIG. 23A) and TEM images (FIG. 23B) to construct the size distribution histograms shown for incubation in the dark for 2 h (FIG. 23C) and irradiation with 500±10 nm light for 2 h (FIG. 23D).

To further confirm that PVP dictates the direction of Au nanostructure growth, an increased amount of PVP (20 times more) was used in the growth solution to promote adsorption onto the top and bottom {111} facets and induce vertical growth. As expected, thicker (h=49±8 nm) Au nanoprisms were obtained with increased PVP concentrations (FIGS. 19A-19D). In FIG. 19A the edges of multiple Au nanoprisms in the stack can be seen through the top nanoprism, indicating the relatively thin dimensions of these nanoprisms obtained from the standard growth solution. In contrast, the prisms were not transparent to the electron beam with increased PVP concentration, as shown by the blue square in FIG. 19C. The thickness measured by AFM (FIG. 5D) was confirmed through SEM by finding nanoprisms oriented perpendicular to the Si wafer substrate (FIG. 19B and FIG. 19D). A series of SEM images were used to determine the average thickness was ca. 22±3 nm for nanoprisms produced with the standard growth solution (FIG. 19B) and ca. 49±8 nm for nanoprisms produced with more PVP (FIG. 19D). These results further confirm that the PVP concentration can be important for regulating the direction of Au nanoprism growth. Subsequent inspection of these thicker nanoprisms with NanoSIMS confirmed the adsorption of PVP onto their top {111} facets with increased surfactant concentrations, as $^{12}C^{14}N^-$ signals were observed from the entire surface of the Au nanoprisms (FIGS. 20A-20C). These results confirm that PVP is performing a unique function as a photocatalytic intermediary, directing the growth trajectory of Au nanostructures by sequestering $AuCl_4^-$ ions from solution and stabilizing hot electrons produced via plasmon excitation at the nanoprism perimeter to preferentially promote lateral growth.

The twin planes exposed along the nanoprism perimeter exhibit structural defects such as kinks, steps, and high-index facets (FIGS. 21A-21D) that impart increased surface energies to these unique structural sites. It has been reported that these defects prompt surfactant adsorption to minimize the surface energy of the metal nanocrystal, as confirmed by the occurrence of $^{12}C^{14}N^-$ signals from adsorbed PVP molecules covering the entire surface of the multiply-twinned nanoparticles (FIG. 3C). Thus, these twin-plane defects capped with PVP serve as the reactive sites for nanomaterials growth.

Figure 26:
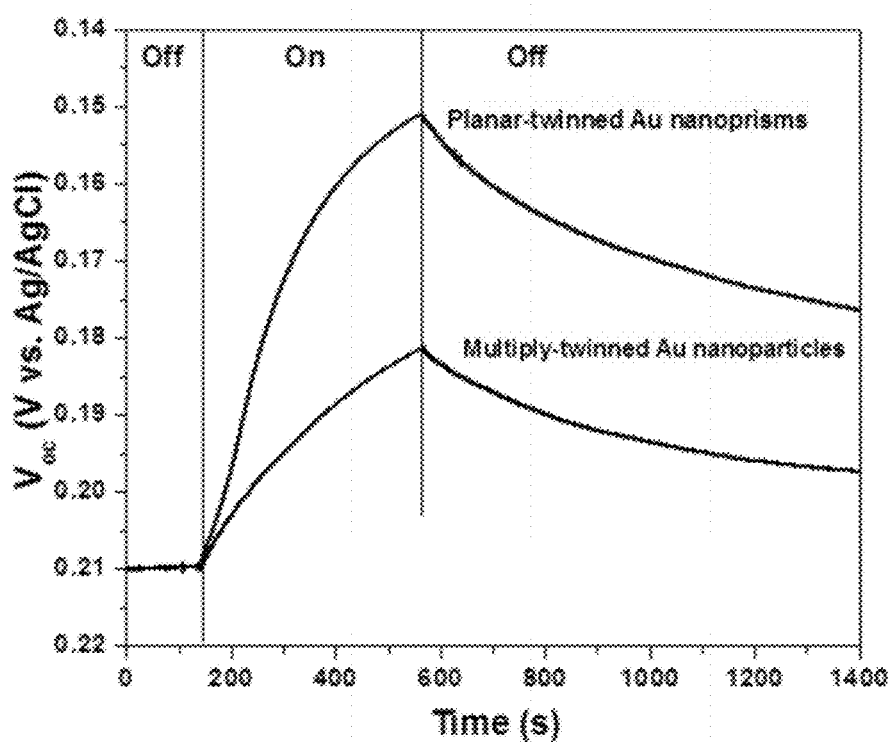
FIG. 26 demonstrates the influence of nanocrystal twinning on open-circuit photovoltage.

Since electrons are known to exhibit substantial mean free paths ($I_{mfp}$~20-150 nm) in Au nanostructures, their transport to the active site is anticipated to constitute a critical step in the plasmon-driven growth mechanism. The inconsistency observed between the physical locations of plasmonic hot spots and the nanoprism growth direction (FIG. 2) implies that these SPR-generated electrons must travel significant distances along the Au nanocrystals prior to catalyzing the reduction of $AuCl_4^-$ species. The ballistic mean free path $I_{mfp}$ of hot electrons can be hindered by scattering off crystal defects, phonons, impurities, etc., with the various contributions adding together according to Matthiessen's rule: $(I_{mfp})^{-1}=(I_{defect})^{-1}+(I_{phonon})^{-1}+(I_{impurity})^{-1}+\ldots$. Thus, twin-plane defects within the Au nanocrystals are anticipated to attenuate the mean free path of these hot electrons by increasing their scattering rate, which ultimately lowers the overall photochemical quantum yield of the reaction. The hot electrons within the planar-twinned nanocrystals should be scattered less than those within the multiply-twinned nanocrystals, and thereby accumulate more readily under optical excitation. Indeed, open-circuit photovoltage measurements demonstrate that the planar-twinned nanoprisms exhibit a much larger photovoltage ($V_{ph}$~60 mV) under visible-light irradiation ($\lambda_{inc}$>495 nm) than that of the multiply-twinned nanocrystals ($V_{ph}$~30 mV) (FIG. 26). Single-nanoparticle growth studies further revealed that the penta-twinned nanoparticles displayed minimal growth under optical excitation, while the increased size of the planar-twinned nanoprisms was clearly evident (FIG. 3, d and e). This observation indicates that SPR excitation manipulates the growth rate of the Au seeds based upon their internal crystal structure. Further analysis of the growth kinetics at the single-nanoparticle level (FIGS. 22A-22F, FIGS. 23A-23D, FIGS. 24A-24B, and FIGS. 25A-25B) unambiguously reveals the pivotal role of plasmon excitation in preferentially promoting the reaction rate of the planar-twinned nanostructures relative to their multiply-twinned counterparts (Table 1).

Figure 27:
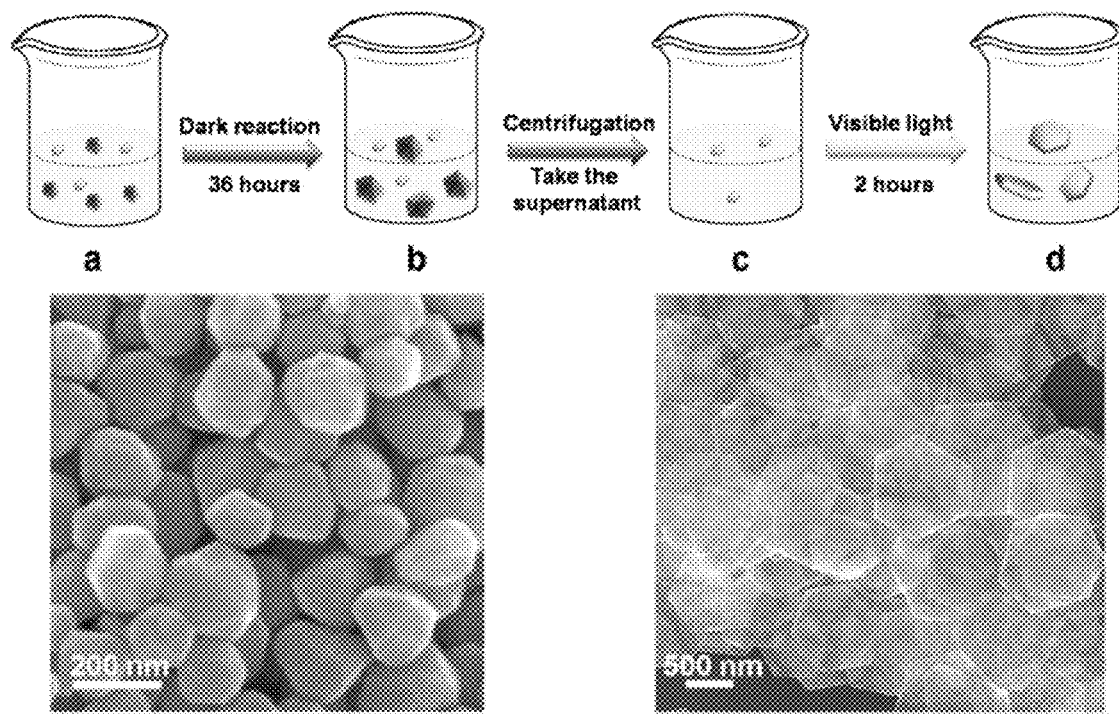
FIG. 27 is a schematic of one embodiments of the seed separation method for the high-yield synthesis of Au nanoprisms. In step (a), the dark reaction is first carried out for 36 h to significantly enlarge the multiply-twinned Au nanocrystals over the planar-twinned nanocrystals due to the different growth rate between these nanocrystals under dark and light conditions (see Table 1). The optimal incubation time typically ranged from 18-36 h. In step (b), after this dark incubation period, the multiply-twinned structures were large enough to be removed from the growth solution by centrifugation at 10,000 rpm for 10 min (as shown in the SEM image on the left). In step (c), the supernatant, now highly enriched in planar-twinned nanocrystals, is then redispersed in a fresh vial and irradiated with 500±10 nm light for 2 h. In step (d), after the reaction, the nanoprisms dominate the distribution (~90% yield by shape) and can be isolated from the reaction solution by centrifugation at 5,000 rpm for 5 min (as shown in SEM image on the right).

The ability to modulate the growth kinetics of structurally distinct Au nanocrystals via SPR excitation inspired the development of a novel seed separation strategy for selectively preparing planar-twinned Au nanoprisms (see FIG. 27). In step (a), the dark reaction is first carried out for 36 h to significantly enlarge the multiply-twinned Au nanocrystals over the planar-twinned nanocrystals due to the different growth rate between these nanocrystals under dark and light conditions (see Table 1). The optimal incubation time typically ranged from 18-36 h. In step (b), after this dark incubation period, the multiply-twinned structures were large enough to be removed from the growth solution by centrifugation at 10,000 rpm for 10 min (as shown in the SEM image on the left). In step (c), the supernatant, now highly enriched in planar-twinned nanocrystals, is then redispersed in a fresh vial and irradiated with 500±10 nm light for 2 h. In step (d), after the reaction, the nanoprisms dominate the distribution (~90% yield by shape) and can be isolated from the reaction solution by centrifugation at 5,000 rpm for 5 min (as shown in SEM image on the right). Here, we exploit the disparate growth kinetics of different twinned nanocrystals to separate the Au seeds (Table 1). The growth rates (v) show remarkable differences under dark and light conditions, as well as between nanocrystal morphologies. All growth rates are given relative to the planar-twinned seeds in the dark ($v_{PT,Dark}$) to enable direct comparison. For instance, the growth of the multiply-twinned decahedrons is about 500 times faster in the light than in the dark, and the decahedron growth rate is about 400 times faster than the planar-twinned nanocrystals in the dark. However, under visible-light irradiation, the growth rate of the planar-twinned nanocrystals is about 10 times faster than that of the decahedrons. Similarly, the growth of the planar-twinned nanocrystals is increased under light irradiation, but much more dramatically than that of the decahedrons, with a growth rate that is about $2\times10^6$ times faster in the light than in the dark. These remarkable differences in growth rate between nanocrystals inspired the development of a new seed separation strategy for producing Au nanoprisms (see FIG. 27).

Figures 4A, 4B:
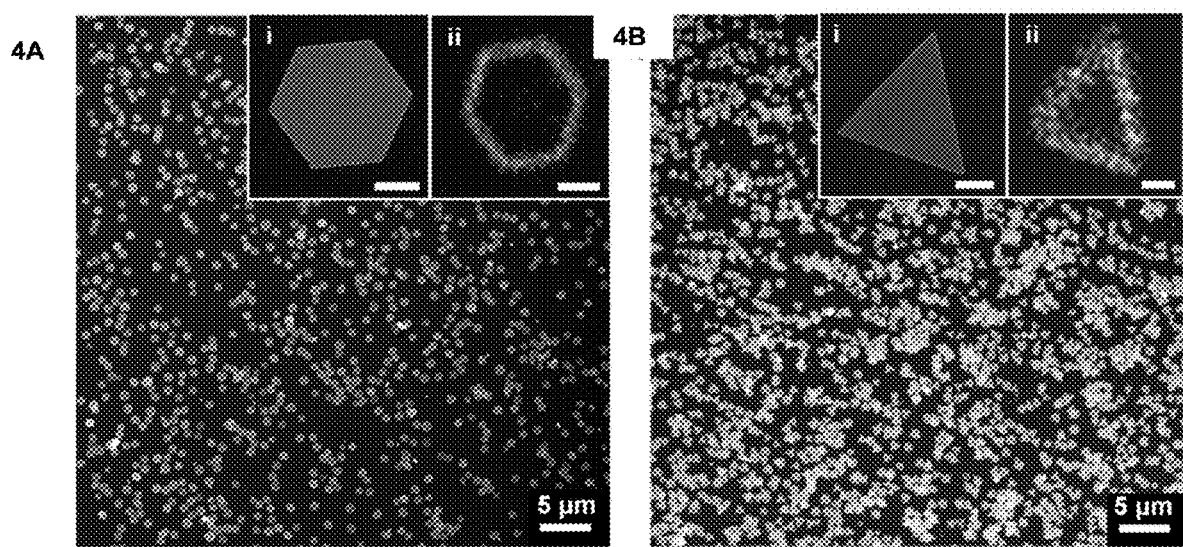
FIGS. 4A-4B demonstrate plasmon-driven synthesis of hexagonal or triangular Au nanoprisms.
Figures 5A, 5B, 5C, 5D:
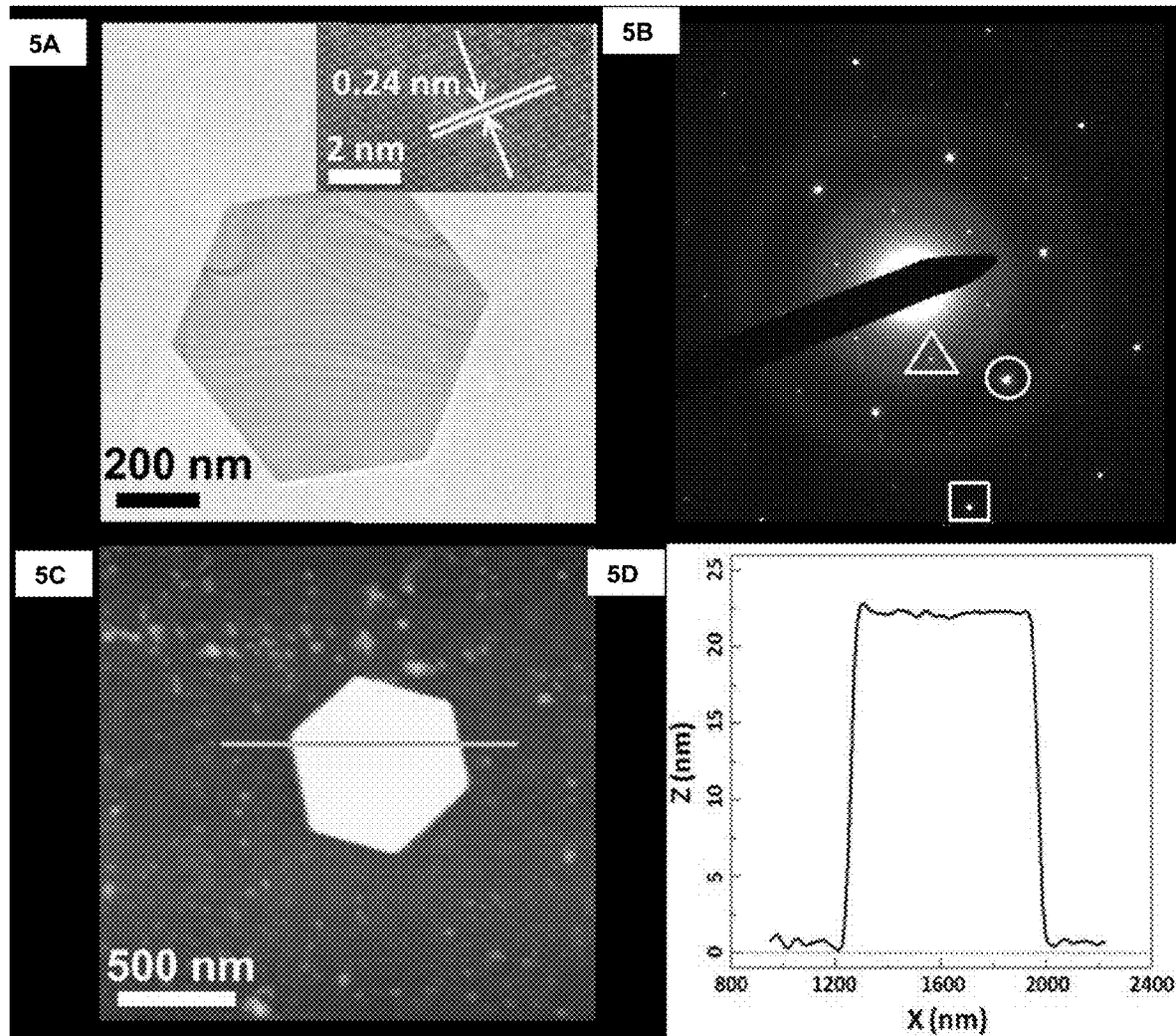
FIGS. 5A-5D demonstrate structural characterization of the Au nanoprisms.
Figure 6A:
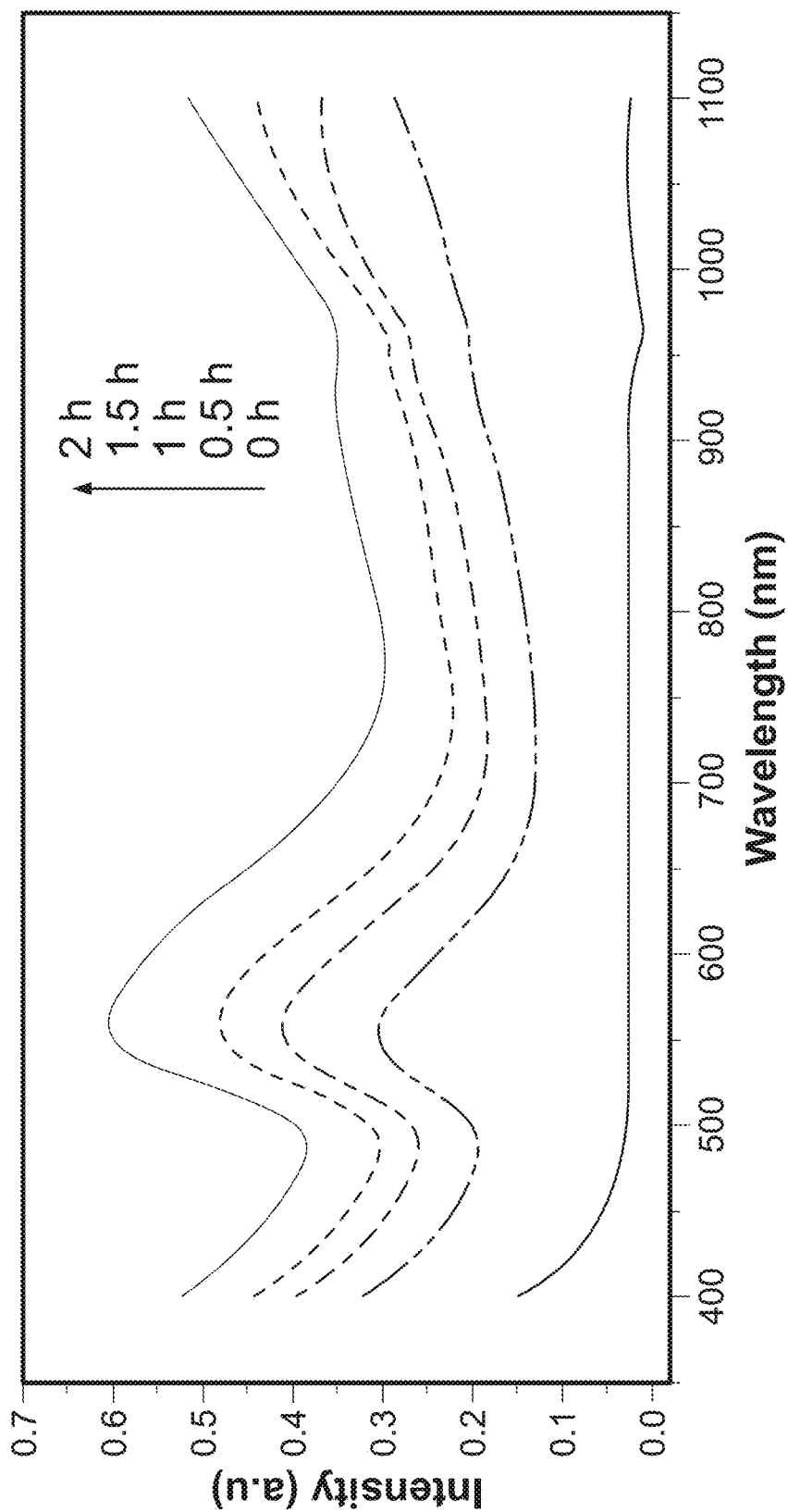
Figures 6B, 6C, 6D, 6E:
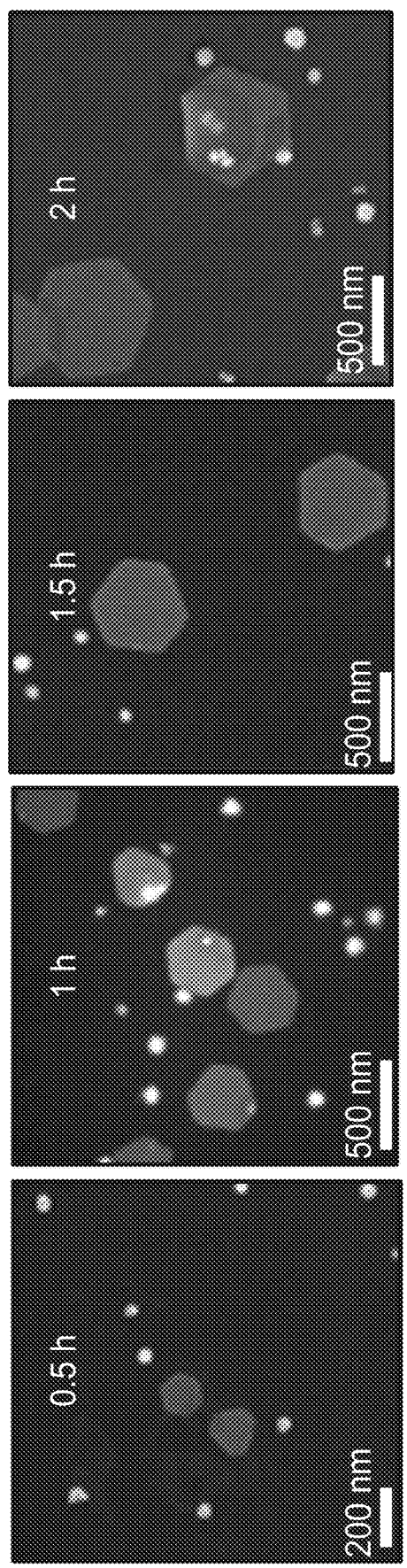
Figure 7:
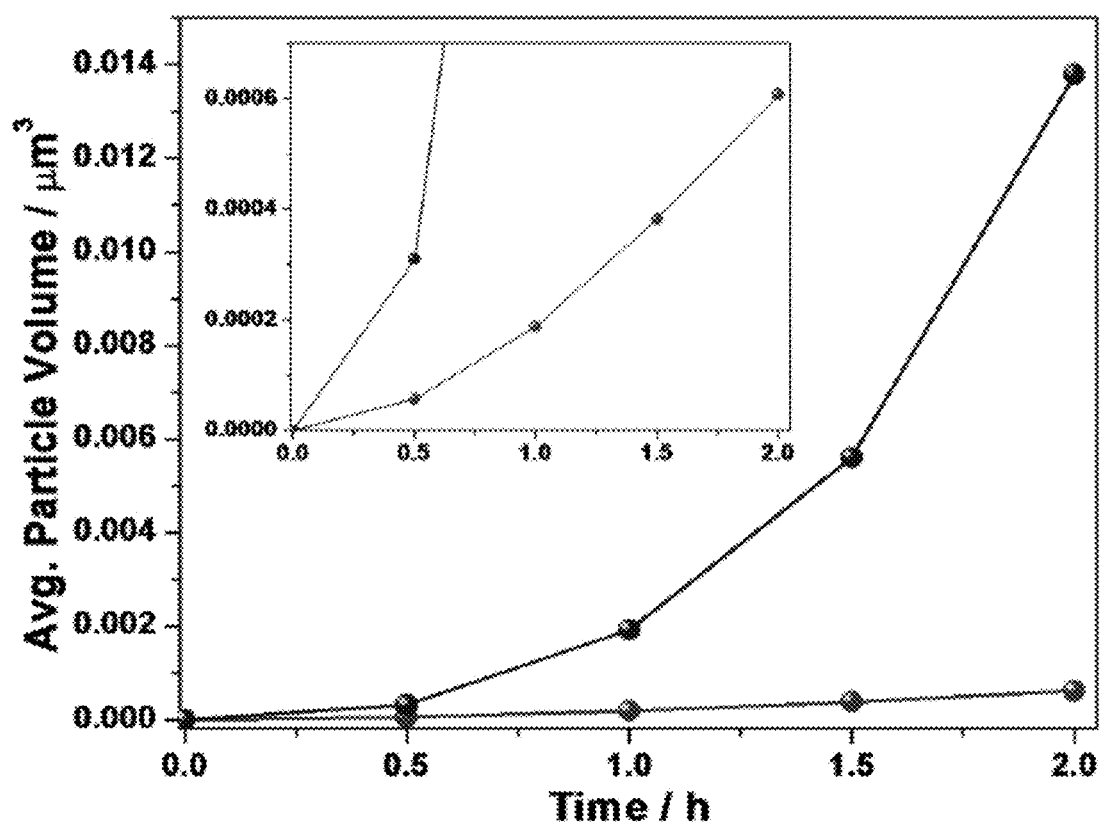
FIG. 7 is a graph of the plasmon-driven growth rate of Au nanostructures obtained by periodically measuring the average diameter of Au nanospheres or the average edge length of Au nanoprisms from SEM images every 30 min over the course of the 2 h reaction (see FIGS. 6A-6M). The average particle volume after each 30 min growth period was then computed based on geometric shape. Inset shows a magnified plot to demonstrate that the pseudo-spherical nanocrystals obey the same trend as the nanoprisms, albeit with significantly reduced overall magnitude.
Figures 8A, 8B, 8C, 8D:
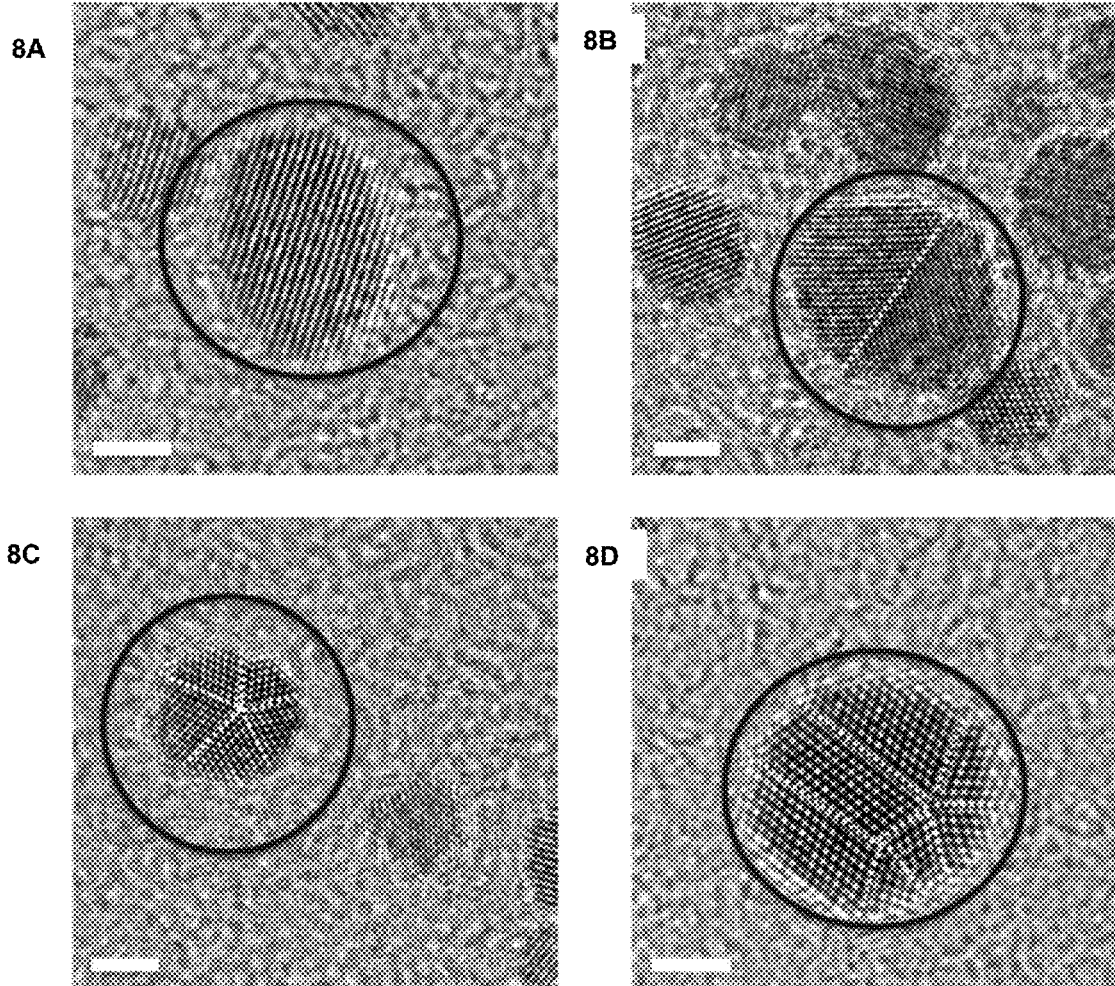
FIGS. 8A-8D demonstrate the identification of diverse nanocrystal structures in the Au seed solution. HRTEM images of various Au seed structures indicated by blue circles.
Figures 24A, 24B:
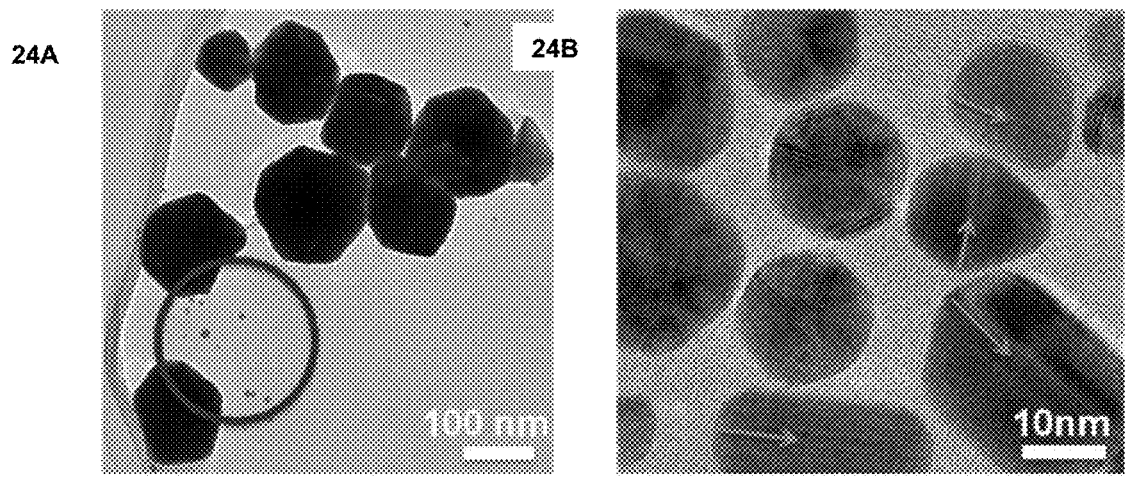
FIGS. 24A-24B demonstrate an investigation of Au seed composition after reaction in the dark.
Figures 25A, 25B:
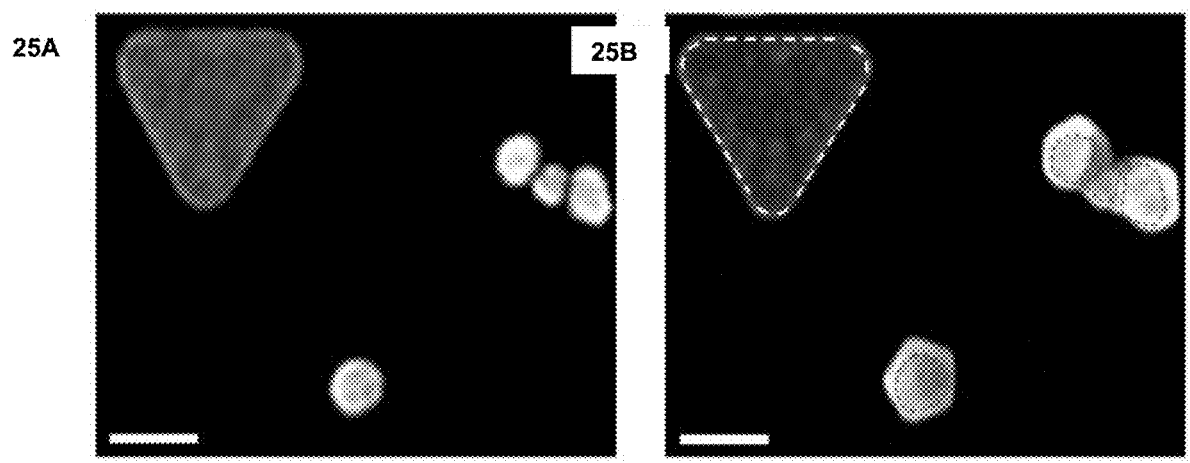
FIGS. 25A-25B demonstrate the results of a single-particle tracking experiment of Au nanoparticles in the dark.
Figure 28:
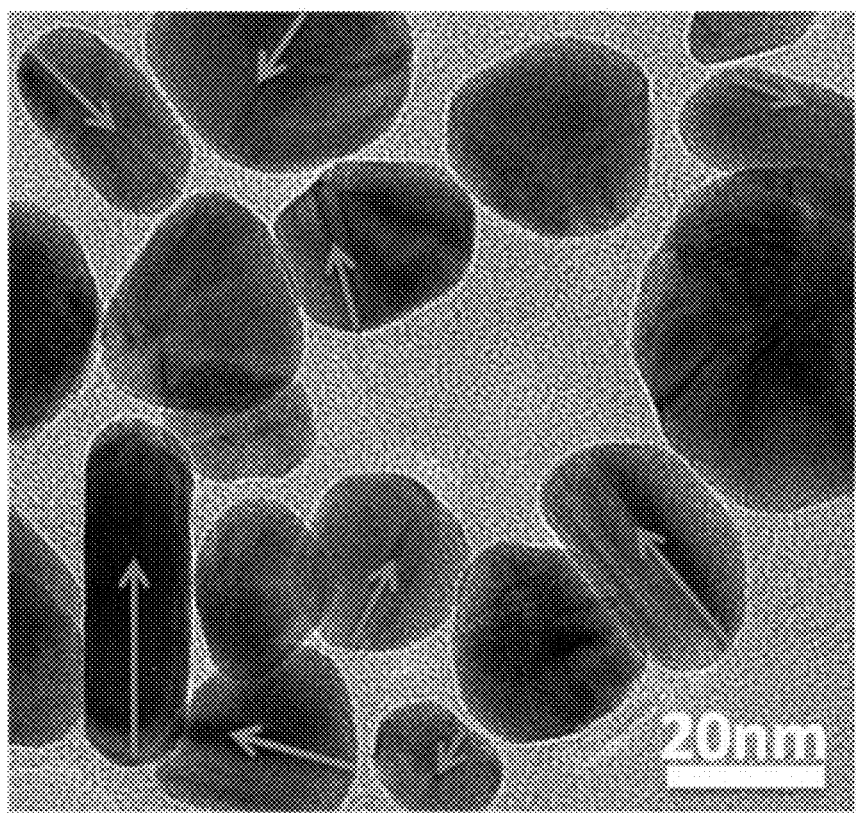
FIG. 28 is a HRTEM image of the Au nanocrystals left in the seed solution after removing the larger multiply-twinned nanocrystals by high-speed centrifugation (10,000 rpm for 10 min) following 36 h of dark reaction. The arrows indicate the planar-twin boundaries.
Figures 29A, 29B, 29C, 29D:
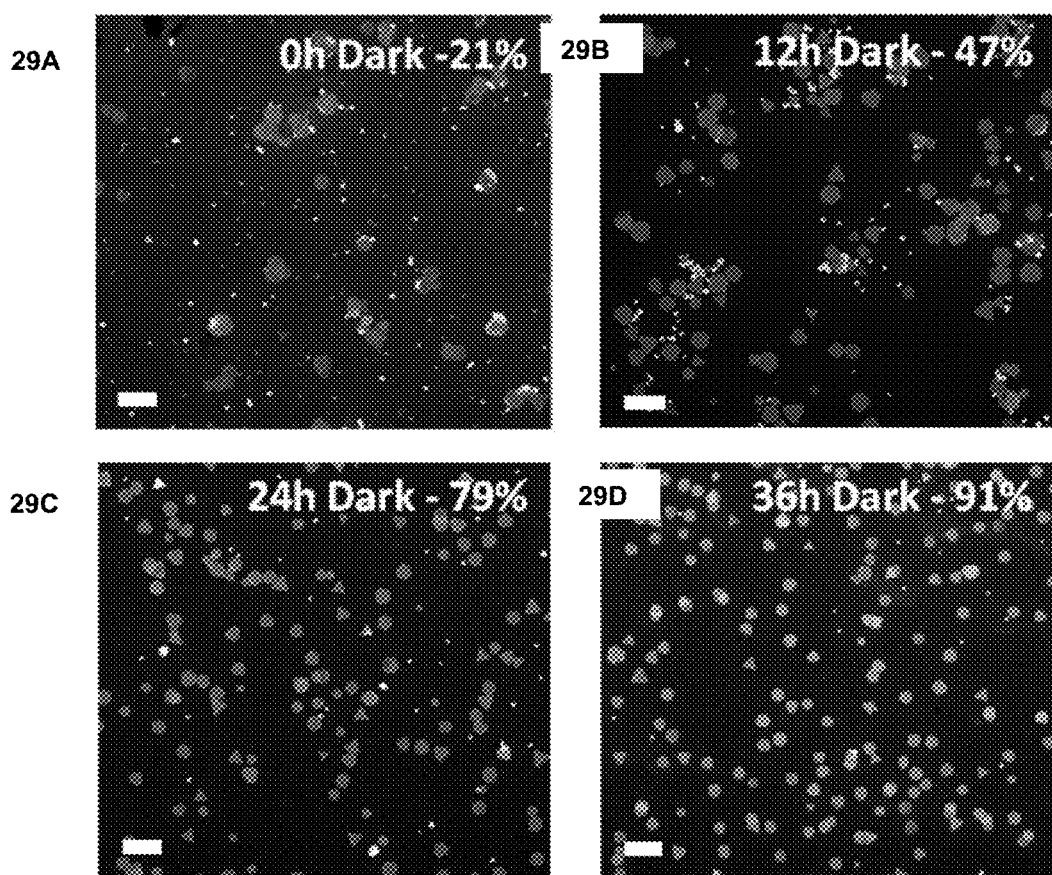
FIGS. 29A-29D demonstrate the influence of dark incubation time on the yield of Au nanoprisms.
Figure 30:
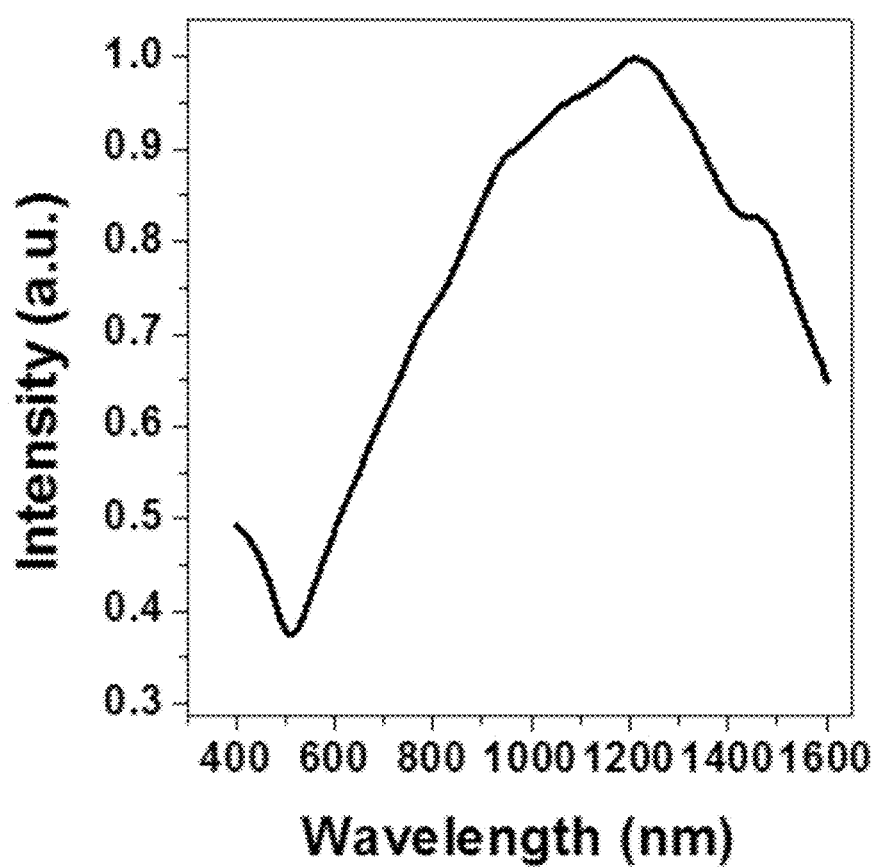
FIG. 30 is an extinction spectrum for the Au nanoprism solution exhibiting a single SPR dipole peak at 1220 nm. The absence of a spherical SPR peak around 550 nm confirms the high yield of nanoprisms obtained using the light-driven method.
Figures 31A, 31B, 31C, 31D, 31E:
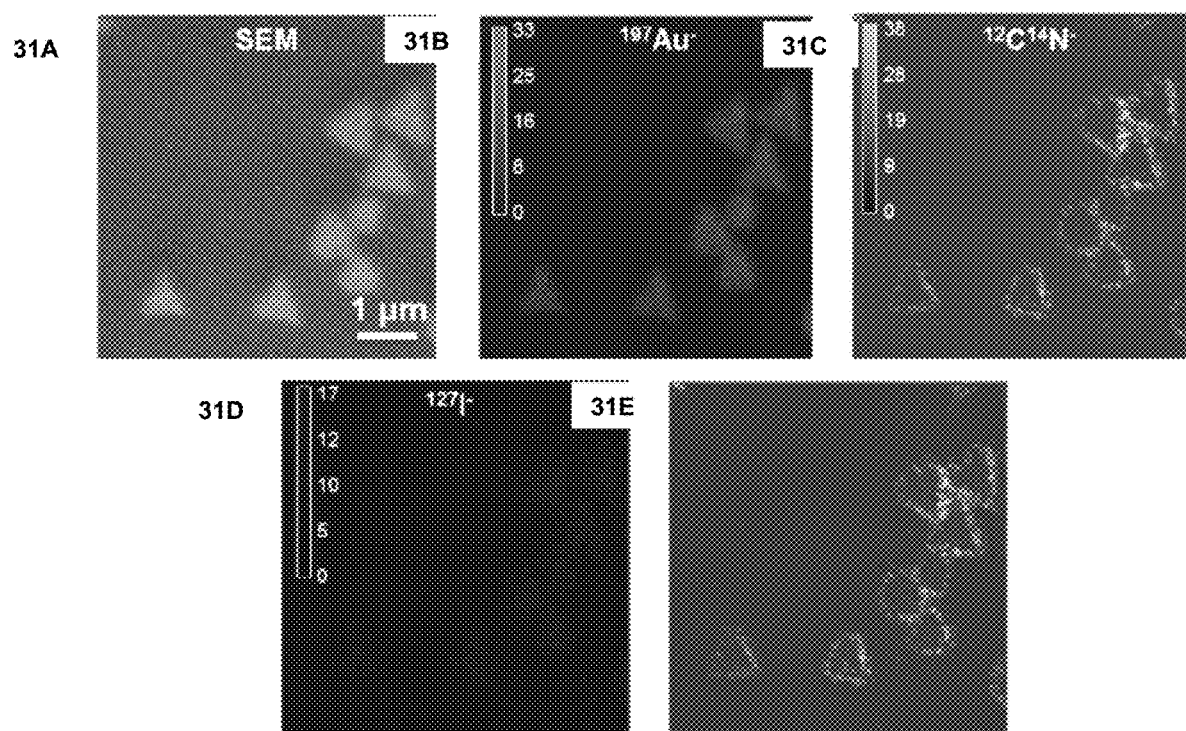
FIGS. 31A-31E depict the NanoSIMS of PVP and iodide distribution on triangular Au nanoprisms.

The growth solution was first incubated under dark conditions to preferentially enlarge the multiply-twinned seeds, while rendering the planar-twinned seeds relatively unreactive as their growth rates are vastly reduced in the dark (FIGS. 24A-24B and FIGS. 25A-25B). These enlarged (d>100 nm) multiply-twinned nanoparticles were then separated from the planar-twinned seeds (d~15 nm) by centrifugation (FIGS. 24A-24B). The supernatant, now highly enriched with planar-twinned nanocrystals (FIG. 28), was then irradiated to produce Au hexagonal nanoprisms in exceptionally high yield (~90%), as shown in FIG. 4A and FIGS. 29A-29D. The monodisperse nature of the final products was also confirmed by UV-Vis spectroscopy (FIG. 30), demonstrating the utility of this unique synthetic approach for producing planar-twinned Au nanoprisms in high purity. Additional architectural control was achieved through the inclusion of iodide to the growth solution (20 μM NaI), which allowed the production of Au triangular nanoprisms with sharp tips (FIG. 4B). Inspection of these nanoprisms by NanoSIMS revealed that $^{127}I^-$ (blue) was distributed across the entire {111} surface (FIG. 4B and FIGS. 31A-31E), while $^{12}C^{14}N^-$ signals (green) from adsorbed PVP were still obtained along the triangular nanoprism perimeter (FIG. 4B). These results are consistent with previous growth studies suggesting that iodide promotes triangular nanoprism growth by passivating Au {111} facets. Such clear delineation between the adsorption locations of these two distinct surface species highlights the merits of combining complementary capping agents to tune nanocrystal growth via this plasmon-driven synthesis strategy.

TABLE 1

Comparison of nanocrystal growth rates under dark and light conditions.

| Au seed structure | Growth rate in the dark | Growth rate under light |
| --- | --- | --- |
| Planar-twinned (PT) Au seeds | $v_{PT,Dark}$ | $v_{PT,Light}$~2 · $10^6 v_{PT,Dark}$ |
| Multiply-twinned (MT) Au seeds | $v_{MT,Dark}$~400$v_{PT,Dark}$ | $v_{MT,Light}$~2 · $10^5 v_{PT,Dark}$ |

Figure 32A:
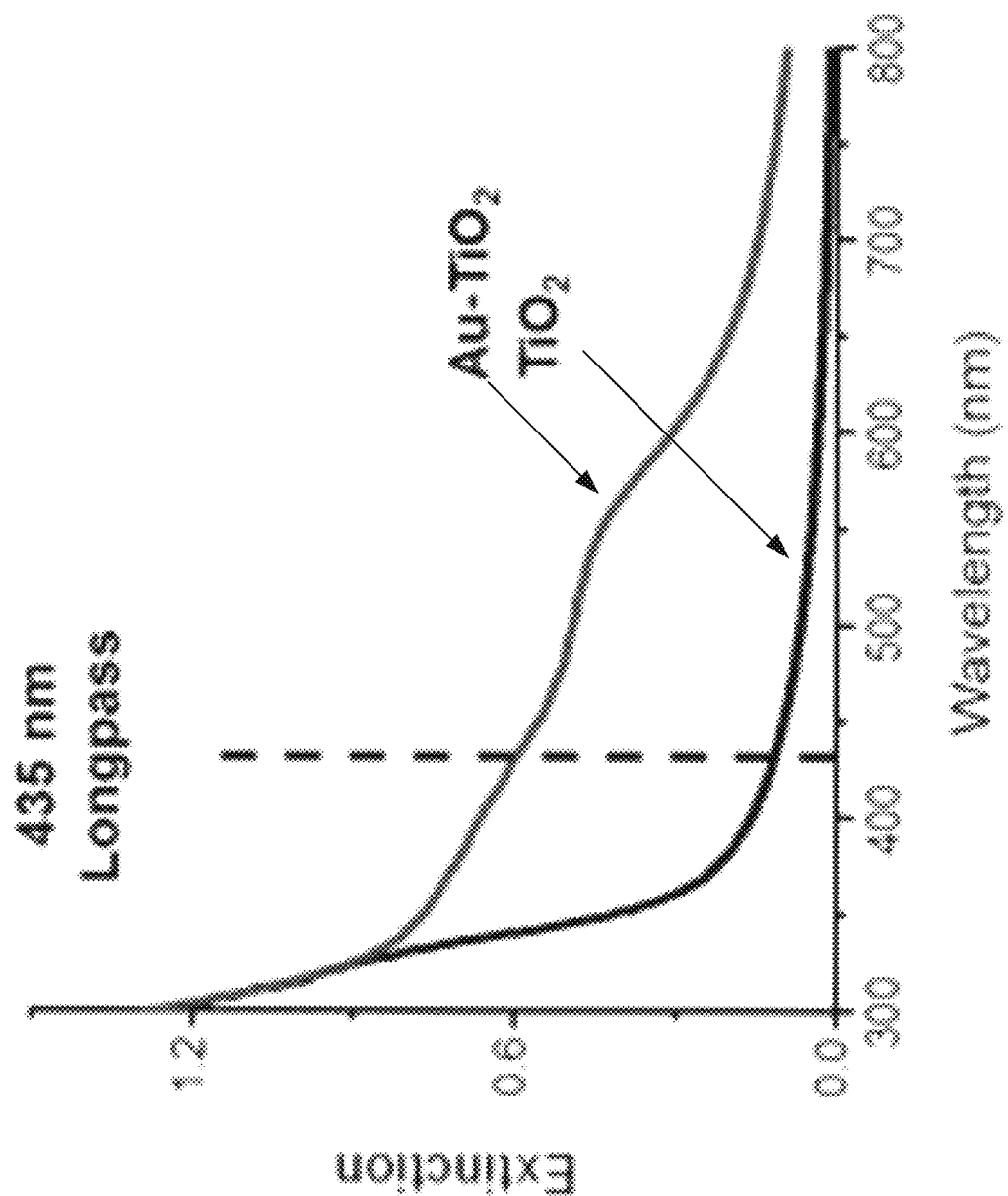

Data in FIGS. 32A-32E show that visible light can drive the photodeposition of platinum (Pt) onto Au—TiO$_2$ nanorod heterostructures. A 300 W Xe lamp equipped with a 515 nm longpass filter was used to irradiate a solution of methanol, H$_2$PtCl$_6$, and the Au—TiO$_2$ nanorod heterostructure suspension. TEM revealed that a significant quantity of new nanoparticles with an average size of ~4 nm formed only on the surfaces of the TiO$_2$ NRs (FIG. 32D) and HRTEM (FIG. 32E). It was also determined using EDX mapping, and XPS that they are Pt(0) crystalline NPs. However, under identical experimental conditions, TiO$_2$ nanorods alone demonstrated no Pt deposition. Without wishing to be bound by a particular theory, it is possible that the excitation of Au SPR prompts the transfer of hot electrons from Au NP across the Schottky barrier formed at the Au—TiO$_2$ interface to the conduction band of TiO$_2$, where they foster the chemical reduction of [PtCl$_6$]$^{2-}$ to form Pt nanoparticles on the surface of the TiO$_2$ (FIGS. 32A-32E). Thus, the photodeposited Pt nanoparticles can serve as a visual map of the "hot electrons" that have been transferred onto the TiO2 surface and been made available for surface reactions.

These findings significantly broaden the scope of noble metal architectures accessible by plasmonic photochemistry through the realization of plasmon-driven Au nanoprism synthesis. Systematic evaluation of the growth mechanism at the single-nanoparticle level reveals that the surfactant PVP serves as a photochemical relay to direct the evolution of anisotropic Au nanoprisms from pseudo-spherical Au seeds: preferential adsorption of PVP onto twin boundaries along the nanocrystal perimeter promotes lateral growth by coupling the photo-generated hot electrons produced on the nanoparticle surface with gold precursors in solution. Our studies elucidate the critical role of adsorbed surface molecules in plasmonic photochemistry, conferring additional chemical functionality to surfactants in the plasmon-driven synthesis of noble metal nanostructures. Further growth studies on individual nanoparticles showed that nanocrystal twinning regulates the reduction kinetics of the plasmon-driven process, revealing a new route to manipulate photochemical reactions via the intrinsic structural features of the nanocrystal itself. This insight inspired a strategy for exploiting SPR excitation to selectively express the planar-twinned seed morphology and produce hexagonal or triangular Au nanoprisms in high yield (~90%). Taken together, these studies provide a molecular-level description of the physicochemical processes that regulate the plasmon-driven synthesis of Au nanoprisms and illustrate the importance of collectively controlling the interaction among light, surfactants, and nanocrystal twinning to effectively harness plasmon-driven photochemistry for the synthesis of noble metal nanostructures.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A method of making noble metal nanoprisms, the method comprising:
    incubating a solution comprising a plurality of seed structures, wherein during the incubating step seed structures are preferentially enlarged, wherein the seed structures are single-crystalline structures, and
    separating the seed structures from the solution based upon the size of the seed structures to produce an enriched growth solution, wherein the size of the seed structure is about 5 to 50 nm;
    irradiating the solution comprising the seed structures, a noble metal precursor, and a photocatalytic intermediary to produce the noble metal nanoprisms having an average thickness of about 10 nm to 30 nm, wherein the photocatalytic intermediary is positively charged.

2. The method of claim 1, wherein the seed structures are planar-twinned structures.

3. The method of claim 1, wherein the seed structures are penta-twinned structures.

4. The method of claim 1, wherein the nanoprism does not comprise silver.

5. The method of claim 1, wherein the noble metal is selected from the group consisting of ruthenium, rhodium, palladium, osmium, iridium, platinum, gold, rhenium, and a combination thereof.

6. The method of claim 1, wherein the noble metal precursor comprises a salt of the noble metal.

7. The method of claim 1, wherein the incubating step is performed at an elevated temperature from about 30° C. to about 40° C.

8. The method of claim 1, wherein the photocatalytic intermediary comprises a γ-lactam ring.

9. The method of claim 1, wherein the photocatalytic intermediary comprises n-methyl-2-pyrrolidone.

10. The method of claim 1, wherein the photocatalytic intermediary comprises polyvinylpyrrolidone.

11. The method of claim 1, wherein the solution further comprises sodium iodide.

12. The method of claim 1, wherein the nanoprisms have a geometry selected from the group consisting of hexagonal nanoprisms and triangular nanoprisms.

13. The method of claim 1, wherein upon introduced to the incubation step the seed structures have an average size of about 5 nm to 15 nm.

14. The method of claim 1, wherein the irradiating step comprises irradiating with light having a wavelength from about 500 nm to 600 nm, and
    wherein the nanoprisms have an average edge length of about 400 nm to 600 nm.

15. The method of claim 1, wherein the irradiating step comprises irradiating with light having a wavelength from about 600 nm to 700 nm, and
    wherein the nanoprisms have an average edge length of about 200 nm to 400 nm.

16. The method of claim 1, wherein the nanoprisms are produced with a yield of 80% to 95% by shape.

* * * * *